(12) United States Patent
Fan et al.

(10) Patent No.: US 11,733,223 B2
(45) Date of Patent: Aug. 22, 2023

(54) NANOSTRUCTURED GAS SENSOR ARRAY AND THE APPARATUS INCORPORATING THE SAME

(71) Applicant: The Hong Kong University of Science and Technology, Hong Kong (CN)

(72) Inventors: Zhiyong Fan, Hong Kong (CN); Zhilong Song, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 384 days.

(21) Appl. No.: 16/947,238

(22) Filed: Jul. 24, 2020

(65) Prior Publication Data
US 2021/0223220 A1    Jul. 22, 2021

Related U.S. Application Data

(60) Provisional application No. 62/995,165, filed on Jan. 16, 2020.

(51) Int. Cl.
*G01N 33/00* (2006.01)
*G01N 27/12* (2006.01)

(52) U.S. Cl.
CPC ..... *G01N 33/0031* (2013.01); *G01N 33/0036* (2013.01); *G01N 33/0067* (2013.01)

(58) Field of Classification Search
CPC .......... G01N 33/0031; G01N 33/0036; G01N 33/0067; G01N 27/127; G01N 33/0034
See application file for complete search history.

(56) References Cited

U.S. PATENT DOCUMENTS

| 4,542,640 A * | 9/1985 | Clifford | G01N 27/122 73/31.06 |
| 2014/0262835 A1* | 9/2014 | Hunter | G01N 27/417 205/785.5 |
| 2019/0369040 A1* | 12/2019 | Drmosh | G01N 33/0037 |

FOREIGN PATENT DOCUMENTS

| WO | WO-0033066 A2 * | 6/2000 | ......... G01N 33/0075 |
| WO | WO-2019099567 A1 * | 5/2019 | ............ G01J 3/4338 |

OTHER PUBLICATIONS

Chen et al.; "Ultra-Low-Power Smart Electronic Nose System Based on Three-Dimensional Tin Oxide Nanotube Arrays"; ACS Nan 2018, 12, 6079-6088; Published May 24, 2018 (Year: 2018).*

* cited by examiner

*Primary Examiner* — Herbert K Roberts
*Assistant Examiner* — Anthony W Megna Fuentes
(74) *Attorney, Agent, or Firm* — S&F/WEHRW

(57) ABSTRACT

A gas sensor array comprises a plurality of metal decorated metal oxide film based on three-dimensional nanostructured templates, each including a porous anodized aluminum oxide (AAO) template and a plurality of metal decorated metal oxide films. The porous AAO substrate has a top surface with top gold electrodes, a bottom surface with bottom gold electrodes and a plurality of pores. Each pore has an interior wall and two openings located on the top surface and the bottom surface respectively for allowing air to enter into the pore. Each metal-decorated metal oxide film comprises a metal oxide film and metal decoration particles. The metal oxide film has an internal surface attaching on a respective interior wall and an external surf-ace being decorated with the metal particles. Each decoration metal is different to provide different sensitivities in response to an environmental gas.

20 Claims, 16 Drawing Sheets

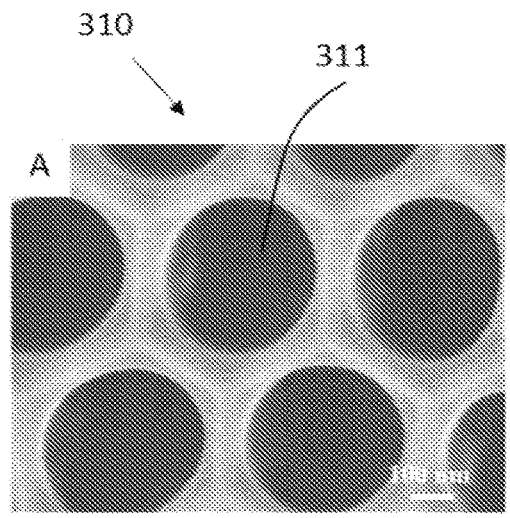 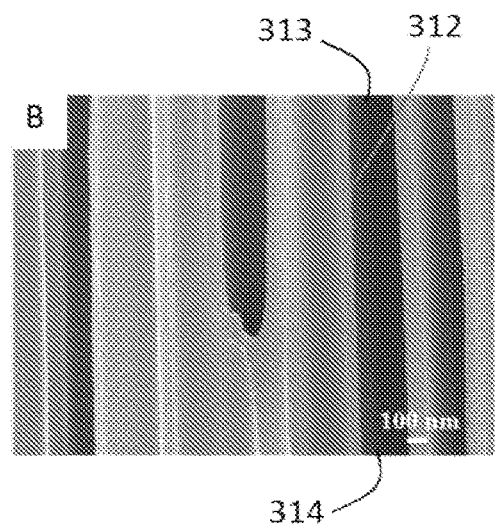
FIG. 3A            FIG. 3B
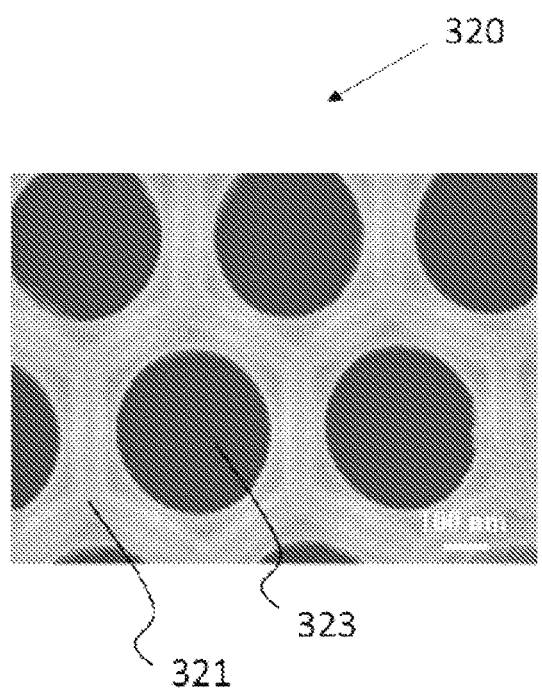
FIG. 3C

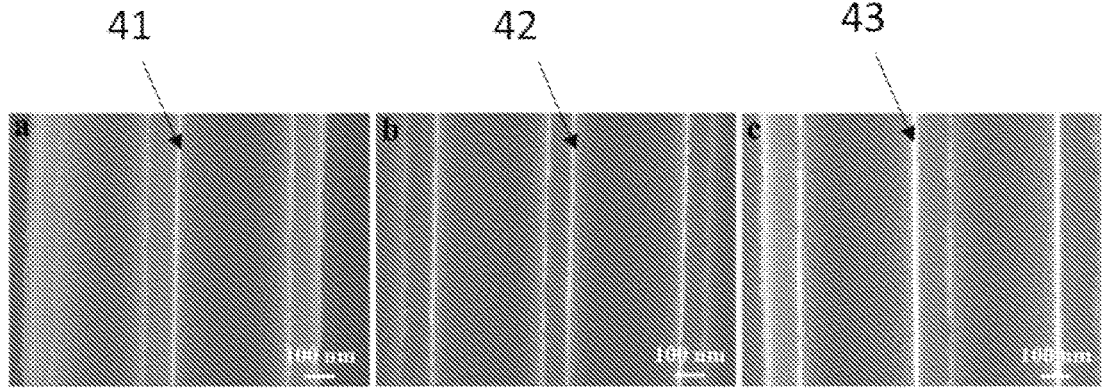
FIG. 4A  FIG. 4B  FIG. 4C
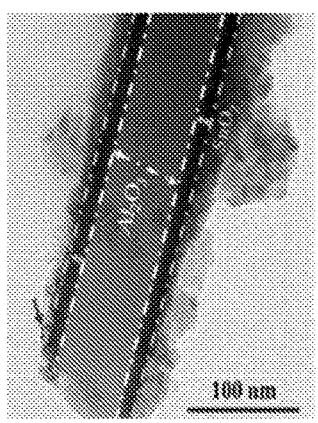 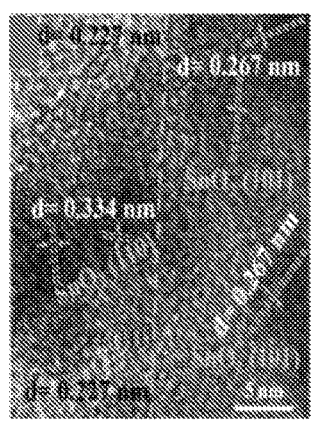 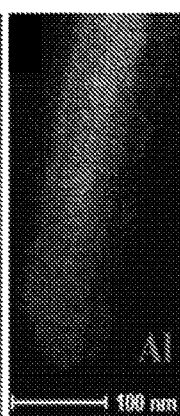 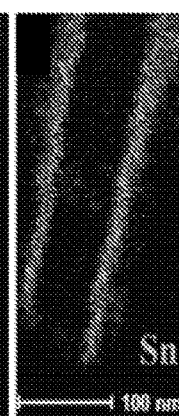 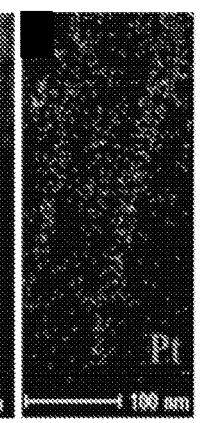
FIG. 5A  FIG. 5B  FIG. 5C  FIG. 5D  FIG. 5E

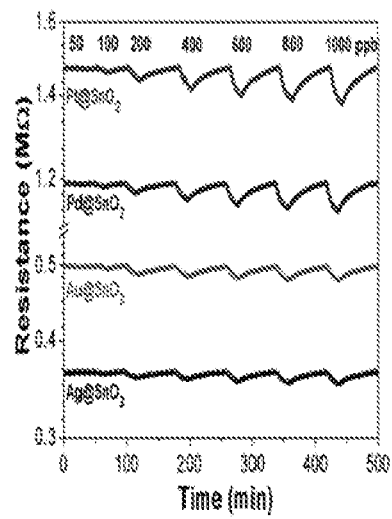 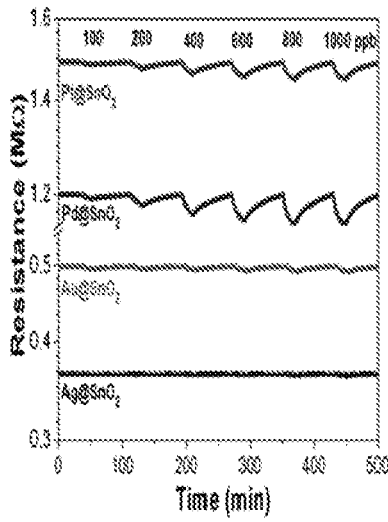 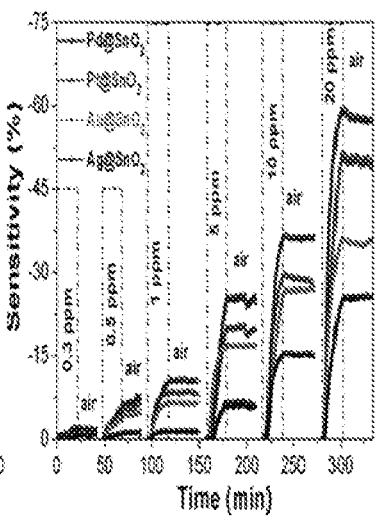
FIG. 7A  FIG. 7B  FIG. 7C
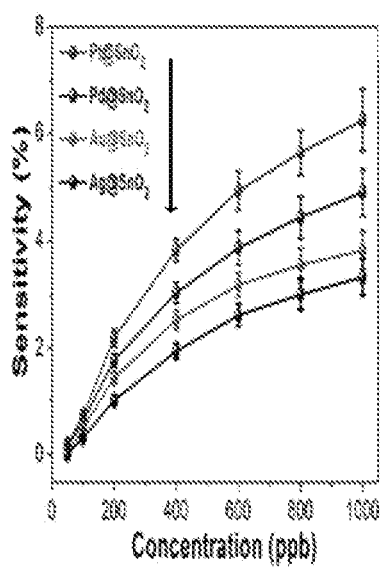 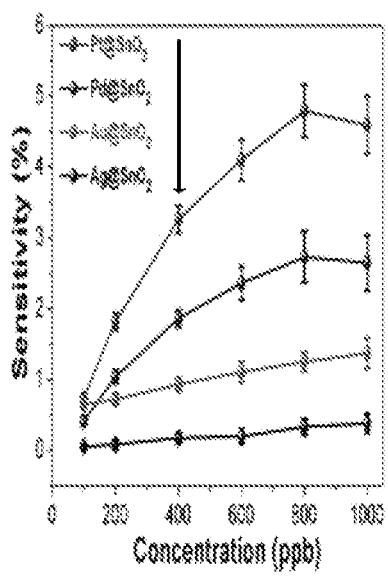 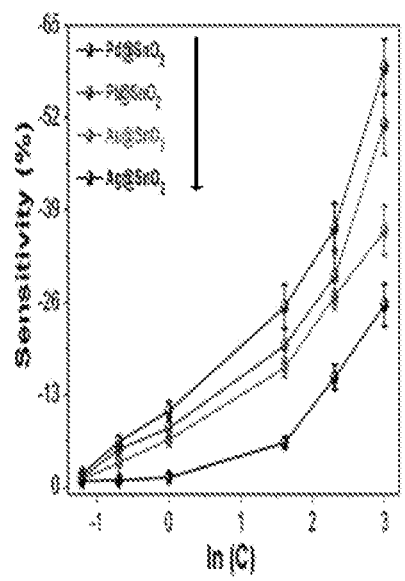
FIG. 7D  FIG. 7E  FIG. 7F

NANOSTRUCTURED GAS SENSOR ARRAY AND THE APPARATUS INCORPORATING THE SAME

CROSS-REFERENCE TO RELATED APPLICATIONS

This application claims the benefit of U.S. Provisional Patent Application No. 62/995,165, filed on Jan. 16, 2020, which is incorporated by reference herein in its entirety.

FIELD OF THE INVENTION

The present disclosure generally relates to a nanostructured gas sensor array, and particularly relates to a 3D nanostructured $SnO_2$ based gas sensor array and the apparatus incorporating the gas sensor array for performing gas detection and concentration level identification.

BACKGROUND OF THE INVENTION

Sensing takes precedence in linking things with the world. With the penetration of Internet of Things (IoT) technology and even great opportunities of the future 5G network into various segments of the buildings, homes and cities, large numbers of data acquisition are needed and thus the sensors with smaller, intelligent, low-power and high-integration are becoming more and more popularity in the market. Smart gas sensors possess the capability in perceiving surrounding environment include detecting chemical analytes, exhaled breath, flammable or explosive gases for the purpose of public and domestic security, gas leakage detection, environmental monitoring and disease diagnosis, playing a vital role in the most important technologies in our daily life. Specific for indoor air quality monitoring and gas leakage detection, gas sensors are required to spatially distribute in a house or a building for long-term continuous monitoring and recognition of the surrounding complicated environment, protecting human beings from the treat of the fire hazardous and explosive gases leakage (e.g., $H_2$, $NO_2$) and parts per billion (ppb)-level chemical analyte (e.g., formaldehyde, toluene) released from the house decorations.

Most gas sensor devices suffer from poor selectivity and high-power consumption, as using heaters is mandatory, not only decreasing stability and service life but also hindering the realization of integration and miniaturization in portable and new generation wireless IoT devices. Moreover, the device system is always powered by the batteries which are required to be replaced or periodically charged due to the finite lifespan, and their limited energy density and capacity, setting a great obstacle for realizing the sensor network deploying that hundreds or thousands of gas sensors are needed in smart home and building application. Therefore, it is highly desirable to develop a self-powered gas sensor system which could successfully realize continuous and high-precision homes/building indoor air quality monitoring for health and safety guarantees. Self-powered systems employing the power source of solar energy, mechanical vibration, bioenergy, wind flow and thermal energy, et al., have been widely presented, which demonstrated as an efficient approach to make the gas sensor nodes self-powered with a possible infinite lifetime. For smart home and/or building applications, solar cells can make full use of the light source and enable directly converting light waves into electrical energy through the photovoltaic effect, considering to be most ideal power source to drive the sensor devices. Indoor-lighting-energy, unaffected by the region, weather and length of day of sunlight, is expected to be a promising indoor power source to overcome the limitation of conventional batteries. Indoor-light-source can generate power density at a level about 100 $\mu W\ cm^{-2}$, which could generate enough power to operate the sensor devices, however, the indoor-light-driven self-powered gas sensor array system for smart home and building application has not been previously reported, mainly due to the challenges on fabrication of the ultralow-power-consumption gas sensor devices and system integration of the functional units.

Accordingly, there is a need in the art to have an ultra low-power-consumption gas sensor device and system. Furthermore, other desirable features and characteristics will become apparent from the subsequent detailed description and the appended claims, taken in conjunction with the accompanying drawings and this background of the disclosure.

SUMMARY OF THE INVENTION

Provided herein is a nanostructured gas sensor array, and particularly relates to a 3D nanostructured $SnO_2$ based gas sensor array and the apparatus incorporating the gas sensor array for performing gas detection and concentration level identification.

An aspect of the present disclosure is to provide a gas sensor array comprising a gas-sensing substrate. The gas-sensing substrate comprises a three-dimensional (3D) porous template made of an electrically insulating material, having a top surface and a bottom surface and comprising a plurality of first pores and a plurality of second pores; a plurality of first metal-decorated metal oxide films, each first metal-decorated metal oxide film being electrically conductive and comprising a first metal oxide film and first metal decoration particles, the first metal oxide film having a first internal surface and a first external surface, the first internal surface attaching on an interior wall of a respective first pore, the external surface being decorated with the first metal decoration particles; and a plurality of second metal-decorated metal oxide films, each second metal-decorated metal oxide film being electrically conductive and comprising a second metal oxide film and second metal decoration particles, the second metal oxide film having a second internal surface and a second external surface, the second internal surface attaching on an interior wall of a respective second pore, the second external surface being decorated with the second metal decoration particles. The first metal decoration particles and the second metal decoration particles are made of different metals such that each first metal-decorated metal oxide film and each second metal-decorated metal oxide film provide different resistances in response to a gas at a concentration such that a first gas sensor formed of respective first metal-decorated metal oxide films and a second gas sensor formed of respective second metal-decorated metal oxide films provide different sensitivities in response to the gas at the concentration for enhancing accuracy of gas identification based on a pattern recognition technique.

In certain embodiments, the 3D porous template further comprises a plurality of third pores and a plurality of fourth pores. The gas-sensing substrate further comprises a plurality of third metal-decorated metal oxide films, each third metal-decorated metal oxide film being electrically conductive and comprising a third metal oxide film and third metal decoration particles, the third metal oxide film having a third internal surface and a third external surface, the third internal surface attaching on an interior wall of a respective third pore, the third external surface being decorated with the third metal decoration particles; and a plurality of fourth metal-decorated metal oxide films, each fourth metal-decorated metal oxide film being electrically conductive and comprising a fourth metal oxide film and fourth metal decoration particles, the fourth metal oxide film having a fourth internal surface and a fourth external surface, the fourth internal surface attaching on an interior wall of a respective fourth pore, the fourth external surface being decorated with the fourth metal decoration particles. The first metal decoration particles, the second metal decoration particles, the third metal decoration particles and the fourth metal decoration particles are made of different metals such that each first metal-decorated metal oxide film, each second metal-decorated metal oxide film, each metal-decorated metal oxide film and each fourth metal-decorated metal oxide film provide different resistances in response to a gas at a concentration such that the first gas sensor, the second gas sensor, a third gas sensor formed of respective third metal-decorated metal oxide films and a fourth gas sensor formed of respective fourth metal-decorated metal oxide films provide different sensitivities in response to the gas at the concentration for enhancing accuracy of gas identification based on the pattern recognition technique.

In certain embodiments, the first, the second, the third, and the fourth metal decoration particles are made of a first metal selected from a group consisting of platinum (Pt), silver (Ag), palladium (Pd), gold (Au), nickel (Ni), copper (Cu), iridium (Ir) and ruthenium (Ru).

Optionally, each of the first, the second, the third, and the fourth metal decoration particles has a diameter between 1 nm and 50 nm.

In certain embodiments, the first metal oxide film, the second metal oxide film, the third metal oxide film and the fourth metal oxide film are made of a metal oxide selected from a group consisting of tin dioxide ($SnO_2$), titanium dioxide ($TiO_2$), zinc oxide (ZnO), nickel(II) oxide (NiO) and iron(III) oxide ($Fe_2O_3$); and each of the first metal oxide film, the second metal oxide film, the third metal oxide film and the fourth metal oxide film has a thickness between 1 nm and 100 nm.

In certain embodiments, the 3D porous template has a honeycomb-like structure and a thickness between 100 nm and 100 μm. The electrically insulating material is aluminium (III) oxide (Al2O3), silicon dioxide (SiO2) or titanium dioxide (TiO2). The plurality of first pores is aligned substantially parallel with each other. The plurality of second pores is aligned substantially parallel with each other; and each of the plurality of first pores and the plurality of second pores has a width between 100 nm and 1 μm.

In certain embodiments, the plurality of first pores is located in a first region of the 3D porous substrate; the plurality of second pores is located in a second region of the 3D porous substrate, the plurality of third pores is located in a third region of the 3D porous substrate; and the plurality of fourth pores is located in a fourth region of the 3D porous substrate.

Another aspect of the present disclosure is to provide a gas detecting apparatus comprising a transmission unit; a microcontroller unit (MCU); a power management unit; and a gas sensor unit formed by packaging the gas sensor array on a sensor PCB. The gas sensor array comprises a plurality of electrodes and a common plane for connecting to the sensor PCB.

In certain embodiments, the plurality of electrodes is deposited on a top surface of the gas sensor array by sputtering deposition using a top electrode mask; and the common plane is deposited on a bottom surface of the gas sensor array by sputtering deposition using a bottom electrode mask.

In certain embodiments, the MCU is configured to identify and quantitatively detect gas species in the environmental gas by performing the pattern recognition technique based on the different sensitivities provided by the first gas sensor, the second gas sensor, the third sensor and the fourth sensor in response to the detected gas species.

Optionally, the pattern recognition technique is a principal component analysis, a support vector machine algorithm, or an artificial neural network.

In certain embodiments, the gas detecting apparatus includes a multiplexer configured to receive a sense voltage across each of the plurality of electrodes sequentially based on a clock signal, and couple the sense voltages to the MCU.

Optionally, the MCU comprises an analog-to-digital converter for converting the sense voltage into digital values. The transmission unit comprises a Bluetooth low energy module for communicatively transmitting the digital values to one or more receiving terminals.

In certain embodiments, the power management unit comprises a solar panel positioned on an exterior surface of the gas detecting apparatus for harvesting indoor light energy, and a rechargeable battery, thereby an infinite lifetime monitoring can be achieved.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which:

FIG. 3A is a scanning electron microscope (SEM) image showing a top view of an anodized aluminum oxide (AAO) template in accordance with certain embodiments of the present disclosure;

FIG. 3B is an SEM image showing a cross-sectional view of the AAO template of FIG. 2A;

FIG. 3C is an SEM image showing a top view of $SnO_2$ thin films in accordance with certain embodiments of the present disclosure;

FIG. 4A is an SEM image showing a cross-sectional view of $SnO_2$ thin films with 5 nm in accordance with certain embodiments of the present disclosure;

FIG. 4B is an SEM image showing a cross-sectional view of $SnO_2$ thin films with 10 nm in accordance with certain embodiments of the present disclosure;

FIG. 4C is an SEM image showing a cross-sectional view of $SnO_2$ thin films with 15 nm in accordance with certain embodiments of the present disclosure;

FIG. 5A is a high-resolution transmission electron microscope (HRTEM) image showing Pt decorated $SnO_2$ thin films in the AAO template in accordance with certain embodiments of the present disclosure;

FIG. 5B is an HRTEM image showing the Pt decorated $SnO_2$ thin films of FIG. 5A with higher magnification;

FIG. 5C is an element mapping for Al in connection with the Pt decorated $SnO_2$ thin films of FIG. 5A;

FIG. 5D is an element mapping for Sn in connection with the Pt decorated $SnO_2$ thin films of FIG. 5A;

FIG. 5E is an element mapping for Pt in connection with the Pt decorated $SnO_2$ thin films of FIG. 5A;

FIG. 7A shows response curves of Pt, Pd, Au and Ag-decorated $SnO_2$ thin films with a thickness of 15 nm under different concentrations of formaldehyde in accordance with certain embodiments of the present disclosure;

FIG. 7B shows the response curves of the Pt, Pd, Au and Ag-decorated $SnO_2$ thin films of FIG. 7A under different concentrations of toluene;

FIG. 7C shows the response curves of the Pt, Pd, Au and Ag-decorated $SnO_2$ thin films of FIG. 7A under different concentrations of $NO_2$;

FIG. 7D shows sensitivities of the Pt, Pd, Au and Ag-decorated $SnO_2$ thin films of FIG. 7A under different concentrations of formaldehyde;

FIG. 7E shows sensitivities of the Pt, Pd, Au and Ag-decorated $SnO_2$ thin films of FIG. 7A under different concentrations of toluene;

FIG. 7F shows sensitivities of the Pt, Pd, Au and Ag-decorated $SnO_2$ thin films of FIG. 7A under different concentrations of $NO_2$;

Figure 1A:
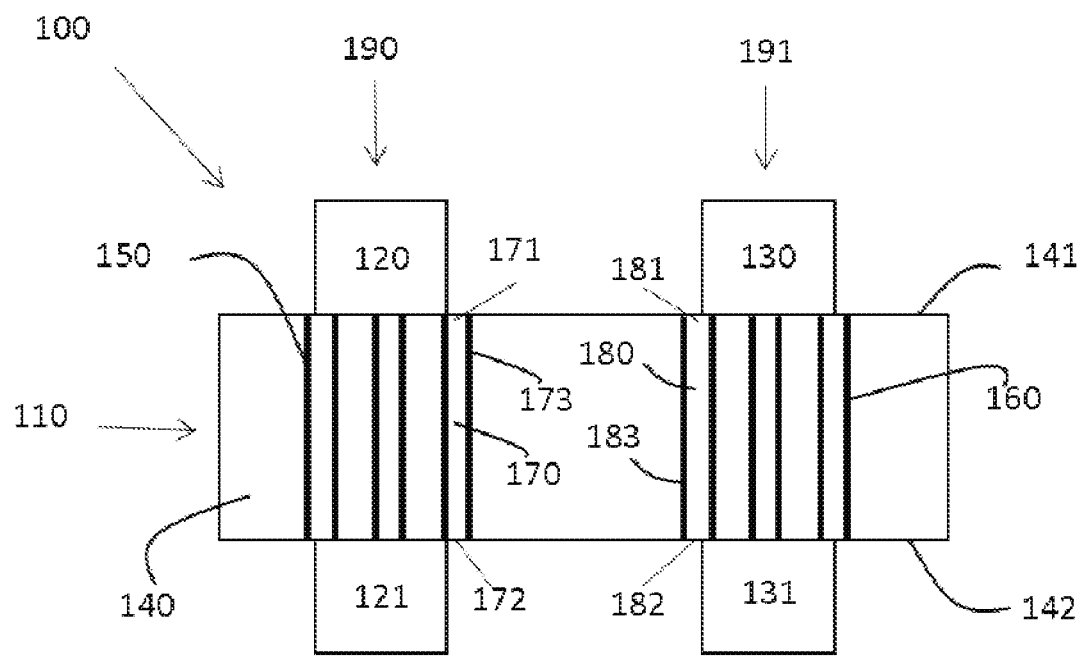
FIG. 1A is a schematic diagram depicting a cross-sectional view of a gas sensor array according to certain embodiments of the present disclosure.

Skilled artisans will appreciate that elements in the figures are illustrated for simplicity and clarity and have not necessarily been depicted to scale.

DETAILED DESCRIPTION OF THE INVENTION

The present disclosure generally relates to a gas sensor array. More specifically, but without limitation, the present disclosure provides a 3D nanostructured $SnO_2$ based gas sensor array and the apparatus incorporating the gas sensor array for performing gas detection and concentration level identification.

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The present invention or any part thereof may be implemented by hardware, software, firmware, middleware, microcode, hardware description languages, or any combination thereof. When implemented in software, firmware, middleware or microcode, the program code or code segments to perform the necessary tasks may be stored in a machine-readable medium such as a non-transitory storage medium. Processor(s) may perform the required tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents via any suitable means including memory sharing, message passing, token passing, network transmission, etc.

The term "cloud" is construed and interpreted in the sense of cloud computing or, synonymously, distributed computing over a network unless otherwise specified. "A server" as used herein, is interpreted in the sense of computing. The one or more "database" may be, for example, electrical circuits, hard disks and/or other solid-state disks for storing data. Generally, a server is equipped with a processor(s) for executing program instructions, and/or storage(s) for storing data. The server may be a standalone computing server or a distributed server in the cloud.

The term "Internet of Things (IoT) device" is used to refer to any device that has an addressable interface (e.g., an Internet protocol (IP) address, a Bluetooth identifier (ID), a near-field communication (NFC) ID, etc.) and can transmit information to one or more other devices over a wired or wireless connection. An IoT device may have an active communication interface, such as a modem, a transceiver, or the like. If a sensor device does not have Internet-connectivity, the device may be connected to a communication device, cell phone, desktop computer, laptop computer, or tablet computer, etc. to form a connected system, such that the connected system can be an IoT device. An IoT device may be controlled or monitored by a central processing unit (CPU), microprocessor, ASIC, or the like, and configured for connection to an IoT network or the Internet.

The benefits, advantages, solutions to problems, and any element(s) that may cause any benefit, advantage, or solution to occur or become more pronounced are not to be construed as critical, required, or essential features or elements of any or all of the claims. The invention is defined solely by the appended claims including any amendments made during the pendency of this application and all equivalents of those claims as issued.

Terms such as "first", "second", and the like are used herein to describe various elements, components, regions, sections, etc., and are not intended to be limiting.

When introducing elements of the present disclosure or the preferred embodiments thereof, the articles "a", "an", and "the" are not intended to denote a limitation of quantity, but rather to denote the presence of at least one of the items being referred to, unless otherwise indicated or clearly contradicted by context. Further, the terms "comprise", "comprising", "including", and "having" are intended to be inclusive and mean that there may be additional elements other than the listed elements.

Certain embodiments of the present disclosure provide a wireless self-powered high-performance 3D nanostructured materials-based gas detecting apparatus, generally including a power management unit, a gas sensor unit, a microcontroller unit, and a transmission unit.

As the gas sensors based on 3D nanostructured materials provide more surface-active site lowering down the activation energy for gas adsorption and activation, which could achieve excellent room-temperature gas-sensing performance with ultralow-power-consumption, the as-fabricated sensor array system can be operated at room temperature, and the average power consumption of each sensor unit was dramatically decreased to 4.3 μW, less than a thousandth of power consumption compared with the commercial $SnO_2$ thin film sensors. Owning to the ultralow-power-consumption senor devices, the self-powered indoor-light-harvesting solar cell can harvest the light power to efficiently drive the senor system and simultaneously get the battery charged, meanwhile, the as-integrated self-powered system can be spatially located in a house, which can achieve continuous and 'infinite-lifetime' remote-monitoring and recognizing the complex gaseous environment (e.g., $H_2$, CO, $CH_4$, $NO_2$, $H_2S$, $SO_2$, $NH_3$, formaldehyde, toluene, benzene, acetone, ethanol, methanol et al.) with pattern recognition techniques using a mobile application. In addition, the wireless data transmission unit using Bluetooth will build up a connection between the sensor array system and the mobile phones, showing the capability of timely remote monitoring and distinguishing the gases, plotting of a geographical distribution map, and even tracing of the gas leakage source for a smart home application.

Figure 1B:
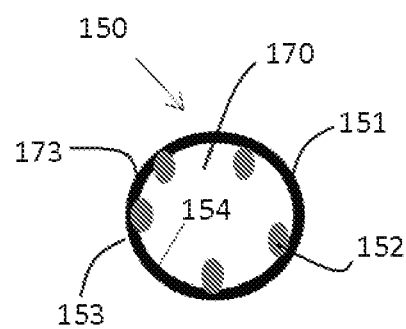
FIG. 1B is a schematic diagram depicting a cross-sectional view of the first metal-decorated metal oxide film of FIG. 1A.
Figure 1C:
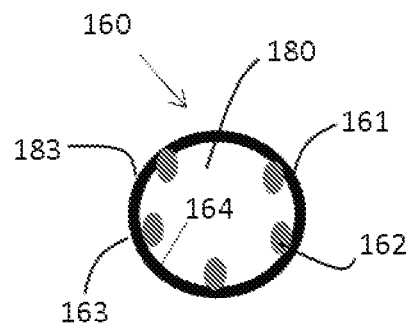
FIG. 1C is a schematic diagram depicting a cross-sectional view of the second metal-decorated metal oxide film of FIG. 1A.

FIGS. 1A-1C depict a gas sensor array 100 in accordance with certain embodiments of the present disclosure. The gas sensor array 100 comprises a gas-sensing substrate 110, a first top electrode 120, a first bottom electrode 121, a second top electrode 130 and a second bottom electrode 131. The gas-sensing substrate 110 comprises a three-dimensional (3D) porous template 140, a plurality of first metal-decorated metal oxide films 150 and a plurality of second metal-decorated metal oxide films 160.

The 3D porous template 140 is made of an electrically insulating material, has a top surface 141 and a bottom surface 142 and comprises a plurality of first pores 170 and a plurality of second pores 180. Each first pore 170 has a first top opening 171 located at the top surface 141 and a first bottom opening 172 located at the bottom surface 142. Each second pore 180 has a second top opening 181 located at the top surface 141 and a second bottom opening 182 located at the bottom surface 142.

As shown in FIG. 1B, each first metal-decorated metal oxide film 150 is electrically conductive and comprises a first metal oxide film 151 and first metal decoration particles 152. The first metal oxide film 151 has a first internal surface 153 and a first external surface 154, the first internal surface 153 attaches on the interior wall 173 of a respective first pore 170, and the external surface 154 is decorated with the first metal decoration particles 152. As shown in FIG. 1C, each second metal-decorated metal oxide film 160 is electrically conductive and comprises a second metal oxide film 161 and second metal decoration particles 162. The second metal oxide film 161 has a second internal surface 163 and a second external surface 164, the second internal surface 163 attaches on the interior wall 183 of a respective second pore 180, the second external surface 163 is decorated with the second metal decoration particles 162.

The first top electrode attaches 120 on the top surface 141 of the 3D porous template 140 and contacts the first metal-decorated metal oxide films 150 at the top surface 141. The first bottom electrode 121 attaches on the bottom surface 142 of the 3D porous template 140 and contacts first metal-decorated metal oxide films 150 at the bottom surface 142 thereby forming a first gas sensor 190. The second top electrode 130 attaches on the top surface 141 of the 3D porous template 140 and contacts the second metal-decorated metal oxide films 160 at the top surface 141. The second bottom electrode 131 attaches on the bottom surface 142 of the 3D porous template 140 contacts the second metal-decorated metal oxide films 160 at the bottom surface 142 thereby forming a second gas sensor 191.

The first metal decoration particles 152 and the second metal decoration particles 162 are made of different metals, such that the first metal-decorated metal oxide films 150 and the second metal-decorated metal oxide films 160 provide different resistances in response to a gas at a concentration, thereby providing the first gas sensor 190 and the second gas sensor 191 with different sensitivity in response to the gas at the concentration for enhancing accuracy of gas identification based on a pattern recognition technique.

In certain embodiments, the first metal decoration particles are made of a first metal selected from a group consisting of platinum (Pt), silver (Ag), palladium (Pd), gold (Au), nickel (Ni), copper (Cu), iridium (Ir) and ruthenium (Ru); and the second metal decoration particles are made of a second metal selected from a group consisting of Pt, Ag, Pd, Au, Ni, Cu, Ir and Ru.

In certain embodiments, each of the first metal decoration particles and the second metal decoration particles has a diameter between 1 nm and 50 nm.

In certain embodiments, the first metal oxide film and the second metal oxide film are made of the same metal oxide.

In certain embodiments, the first metal oxide film and the second metal oxide film are made of a metal oxide selected from a group consisting of tin dioxide ($SnO_2$), titanium dioxide ($TiO_2$), zinc oxide (ZnO), nickel(II) oxide (NiO) and iron(III) oxide ($Fe_2O_3$).

In certain embodiments, each of the first metal oxide film and the second metal oxide film has a thickness between 1 nm and 100 nm.

In certain embodiments, the 3D porous template is a 3D porous AAO template.

In certain embodiments, the electrically insulating material is aluminium (III) oxide ($Al_2O_3$), silicon dioxide ($SiO_2$) or titanium dioxide ($TiO_2$)

In certain embodiments, the plurality of first pores is aligned substantially parallel with each other; and the plurality of second pores is aligned substantially parallel with each other.

In certain embodiments, each of the plurality of first pores and the plurality of second pores has a width between 100 nm and 1 µm.

In certain embodiments, the plurality of first pores is located in a first region of the 3D porous template; and the plurality of second pores is located in a second region of the 3D porous template.

In certain embodiments, the gas-sensing substrate includes 2-10 types of the metal-decorated metal oxide film. Each type of the metal-decorated metal oxide film is decorated by metal decoration particle made of a particular metal.

Figure 2A:
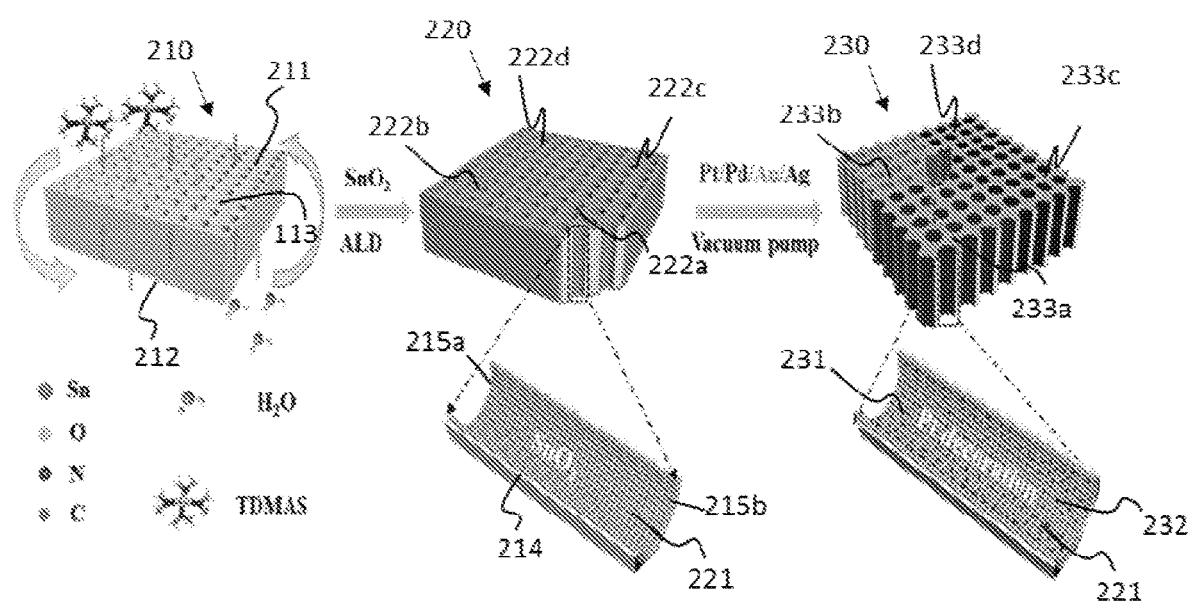
FIG. 2A is a schematic diagram depicting a process for fabricating a gas-sensing substrate by atomic layer deposition and vacuum pumping for metal decoration based on a 3D porous AAO template in accordance with certain embodiments of the present disclosure.

FIG. 2A is a schematic diagram depicting a process for fabricating a gas-sensing substrate by atomic layer deposition of $SnO_2$ and vacuum pumping for metal decoration in accordance with certain embodiments of the present disclosure. A 3D porous AAO template 110 is provided. The 3D porous AAO template 210 has top surface 211, a bottom surface 212 and a plurality of pores 213, and each pore 213 has an interior wall 214 and two openings 215a, 215b located on the top surface 211 and the bottom surface 212 respectively for allowing gases to be determined to enter into the pore 213. Then, a $SnO_2$ thin film 221 is deposited on the interior wall 214 of each pore 213 by atomic layer deposition thereby forming a $SnO_2$-coated 3D porous AAO template 120.

The $SnO_2$-coated 3D porous AAO template 220 is equally divided into four regions 222a, 222b, 222c and 222d. The $SnO_2$ thin film 221 within each pore 213 in the region 222a is decorated with Pt particles 231 by a vacuum pumping method with a shadow mask to form a Pt-decorated $SnO_2$ thin film 232. Under the similar vacuum pumping method, the $SnO_2$ thin film 220 within each pore 213 in the region 222b is decorated with Pd particles to form a Pd-decorated $SnO_2$ thin film, the $SnO_2$ thin film 220 within each pore 213 in the region 222c is decorated with Au particles to form an Au-decorated $SnO_2$ thin film, and the $SnO_2$ thin film 120 within each pore 213 in the regions 222d is decorated with Ag particles to form an Ag-decorated $SnO_2$ thin film 232, thereby forming a gas-sensing substrate 230 having four gas-sensing regions 233a, 233b, 233c, 233d. The Pt-decorated gas-sensing region 233a includes Pt-decorated $SnO_2$ thin films, the Pd-decorated gas-sensing region 233b includes Pd-decorated $SnO_2$ thin films, the Au-decorated gas-sensing region 233c includes Au-decorated $SnO_2$ thin films, and the Pt-decorated gas-sensing region 233d includes Pt-decorated $SnO_2$ thin films. As the Pt, Pd, Au and Ag particles are adhered on the $SnO_2$ thin films 232 respectively and affect the $SnO_2$ thin film 232 differently, Pt, Pd, Au and Ag-decorated $SnO_2$ thin films provide different resistances in response to a gas at a concentration. Accordingly, the four gas-sensing regions 233a, 233b, 233c, 233d provide different sensitivities in response to a gas at a concentration and are responsible for detecting particular gases and identifying their concentrations.

Figure 2B:
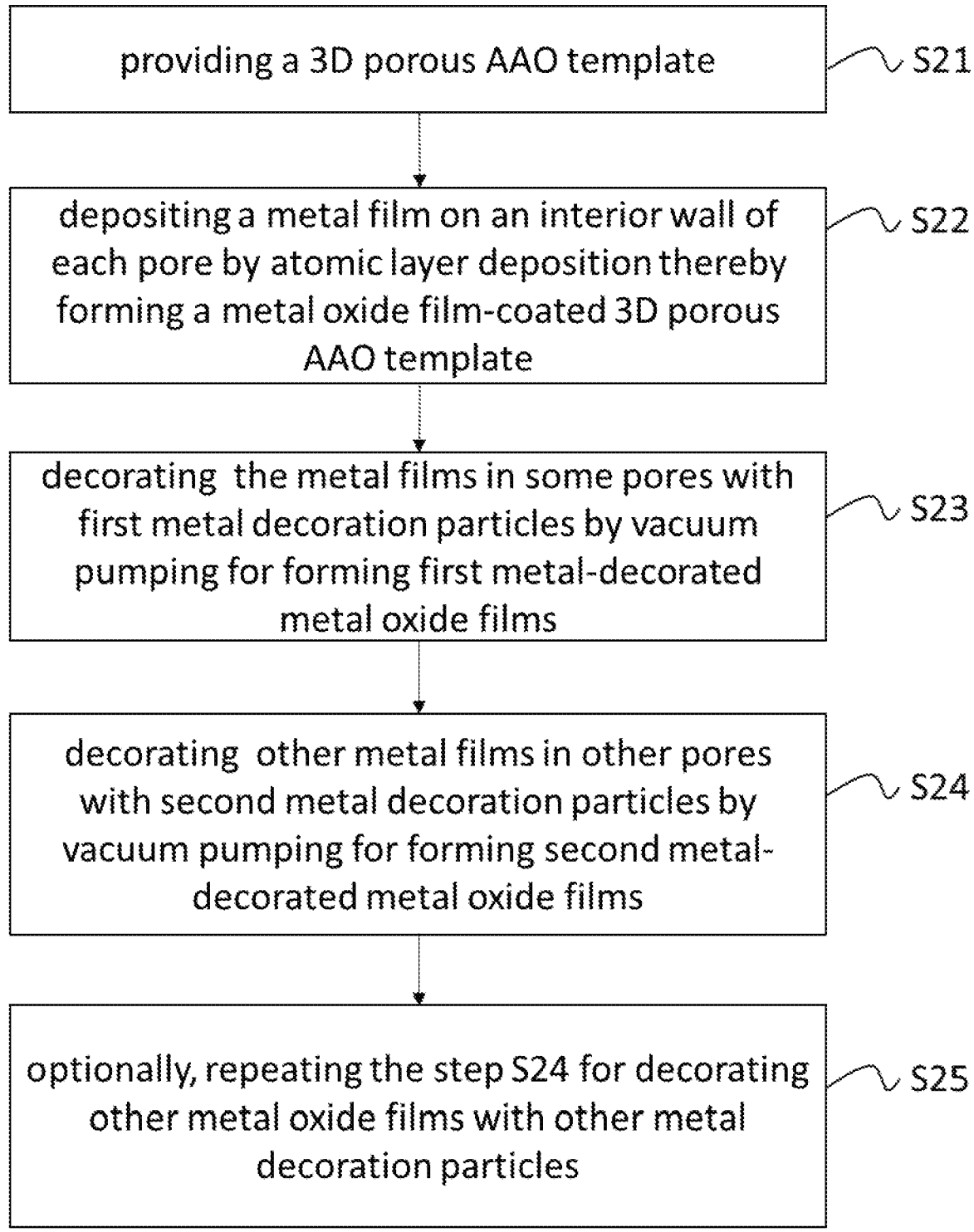
FIG. 2B is a flow chart depicting a method for fabricating a gas-sensing substrate based on 3D porous AAO template in accordance with certain embodiments of the present disclosure.

FIG. 2B is a flow chart depicting a method for fabricating a gas-sensing substrate in accordance with certain embodiments of the present disclosure. In step S21, a 3D porous AAO template having a plurality of pores is provided. In step S22, a metal oxide film is deposited on an interior wall of each pore by atomic layer deposition thereby forming a metal oxide-coated 3D AAO template. In step S23, the metal oxide films in some pores are decorated with first metal decoration particles by vacuum pumping for forming first metal-decorated metal oxide films within the 3D porous AAO template. In step S24, other metal oxide films in other pores are decorated with second metal decoration particles by vacuum pumping for forming second metal-decorated metal oxide films within the 3D porous AAO template. In step S25, optionally, repeating the step S24 for decorating other metal oxide films with other metal decoration particles until that the gas-sensing substrate is formed.

Accordingly, using the atomic layer deposition to construct a 3D porous substrate together with metal decoration, the operating temperature of the gas sensor array is reduced to room temperature and the power consumption is also reduced. In certain embodiments, a metal-decorated $SnO_2$ based AAO template used in the gas sensor array only consumes an average power of 4.3 µW, which is less than a thousandth of the power consumption of a commercial $SnO_2$ thin film sensor.

In certain embodiments, low temperature ALD (~150° C.) is employed because of the uniform deposition with controllable thickness even on complex 3D surfaces, which is crucial for maintaining the device consistency and future mass production. In the ALD process, alternative pulses of two precursor vapor (TDMAS and $H_2O$) and purge gas are introduced into the reactor, resulting in thin film growth due to self-saturating reactions with accessible surface groups of AAO, resulting in a self-limited growth of a monolayer of $SnO_2$ thin films. After finishing the $SnO_2$ nanoparticles deposition, four kinds of metal (Pt, Pd, Au and Ag) with the average sizes of 5 nm are decorated using a vacuum pumping method with a shadow mask.

In certain embodiments, nano-scale $SnO_2$ films are deposited in the 3D AAO template by ALD. A specific cycle of the ALD includes: using tetrakis(dimethylamido)tin as the tin source; opening the ALD tin source valve for 100 ms, closing the pump valve, allowing the tin source to stay in the chamber for 5 s, opening the pump valve for 20 s for cleaning; closing the pump valve; allowing the precursor source to stays in the cavity for 5 s; and opening the pump valve for 25 s for cleaning. The $SnO_2$ films with different thicknesses are obtained through applying different numbers of the specific cycle.

In certain embodiments, the parameters of a cycle of the ALD are shown in Table 1.

TABLE 1

Thin film: $SnO_2$
Cycle number: 10–4000

| precursor | Pulse (ms) | Cleaning (s) | Staying (s) | Source bottle heating temperature | Deposition temperature | Quality controller (sccm) |
|---|---|---|---|---|---|---|
| Tetrakis (dimethyl-amido)tin | 100 | 20 | 5 | 70 | 150 | 20 |
| $H_2O$ | 20 | 25 | 5 | room temperature | | |
| Experimental results | | | Deposition rate: 0.10 nm/cycle | | | |

In certain embodiments, different regions of a metal oxide film coated AAO template are decorated with different metal nanoparticles by a vacuum pumping method. By controlling the concentration and amount of metal nanoparticles in the vacuum pumping method, the amount of the metal nanoparticles in the metal oxide film coated AAO template can be easily controlled.

Figure 3D:
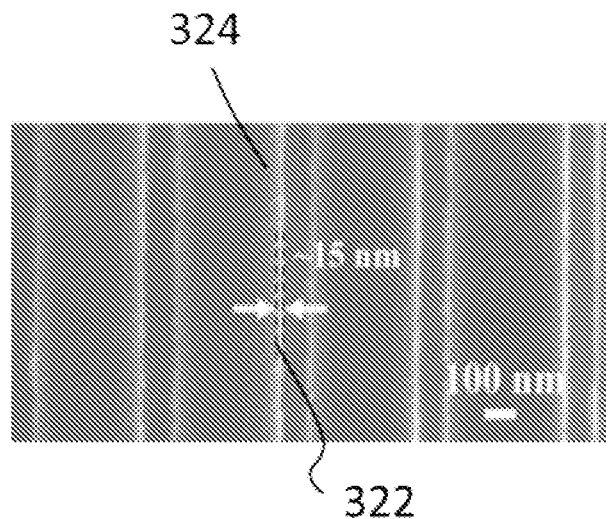
FIG. 3D is an SEM image showing a cross-sectional view of the $SnO_2$ thin films of FIG. 3A.
Figure 3E:
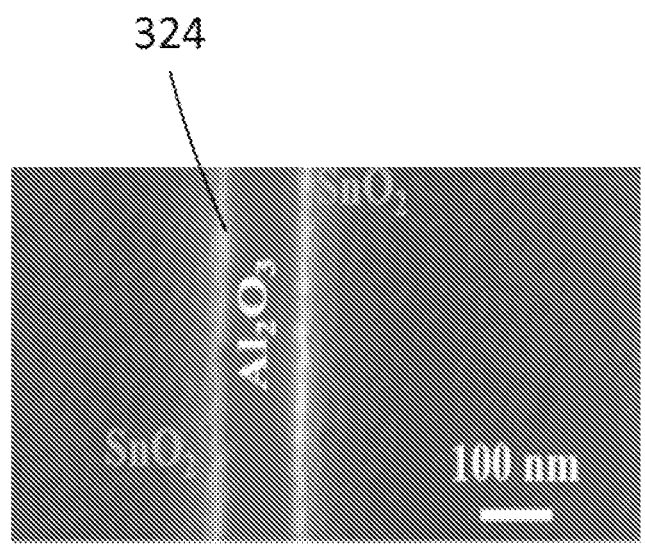
FIG. 3E is an SEM image showing a cross-sectional view of the $SnO_2$ thin films FIG. 3A with higher magnification.

FIGS. 3A and 3B show a porous AAO template 310 having a plurality of pores 311 in accordance with certain embodiments. Each pore 311 has an interior wall 312, a top opening 313 and a bottom opening 314.

FIGS. 3A-3C show a $SnO_2$ film coated-porous AAO template 320 in accordance with certain embodiments. The $SnO_2$ coated-porous AAO template 320 comprises a porous AAO template 321 and $SnO_2$ thin films 322 formed on interior walls 324 of pores 323 of the porous AAO template 321.

FIGS. 4A-4C show $SnO_2$ thin films 41 having a thickness of 5 nm, $SnO_2$ thin films 42 having a thickness of 10 nm and $SnO_2$ thin films 41 having a thickness of 15 nm respectively. In order to achieve large surface-to-volume ratio and high-performance room-temperature gas sensors, the 3D porous AAO template has a thickness of 40 μm, a pitch of 500 nm and an average pore size of 400 nm for providing good support for uniform $SnO_2$ layer deposition.

FIG. 5A shows a Pt-decorated $SnO_2$ thin film attached on an interior wall of a pore of an AAO template. FIG. 5B shows the Pt-decorated $SnO_2$ thin films with higher magnification. FIGS. 5C-5E show element mappings for Al, Sn and Pt in connection with the Pt-decorated $SnO_2$ thin film. The Pt particles are dispersed on the surface of the $SnO_2$ thin film.

Figure 6A:
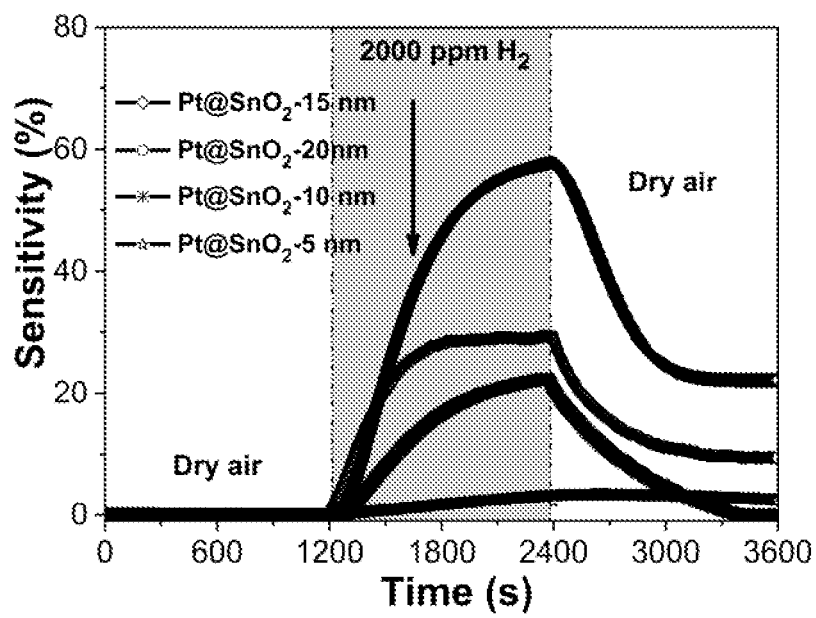
FIG. 6A shows the sensitivity of Pt decorated $SnO_2$ thin films with thickness of 5, 10, 15 and 20 nm under hydrogen versus time in accordance with certain embodiments of the present disclosure.
Figure 6B:
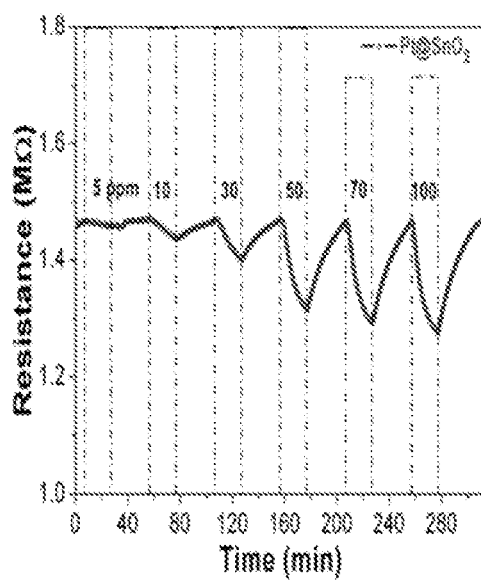
FIG. 6B shows the resistance of Pt decorated $SnO_2$ thin films under different concentrations of hydrogen in accordance with certain embodiments of the present disclosure.
Figure 6C:
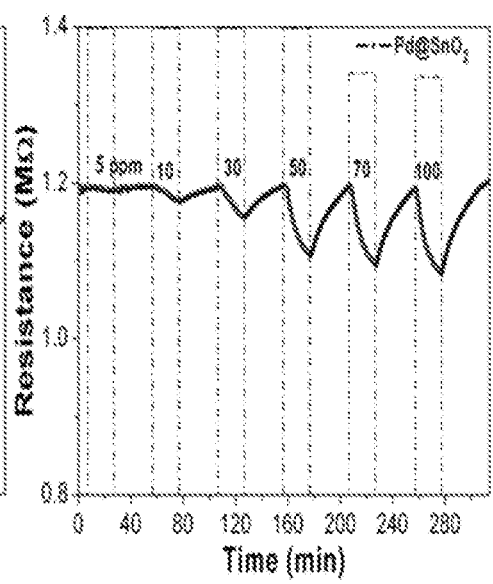
FIG. 6C shows the resistance of Pd decorated $SnO_2$ thin films under different concentrations of hydrogen in accordance with certain embodiments of the present disclosure.
Figures 6D, 6E:
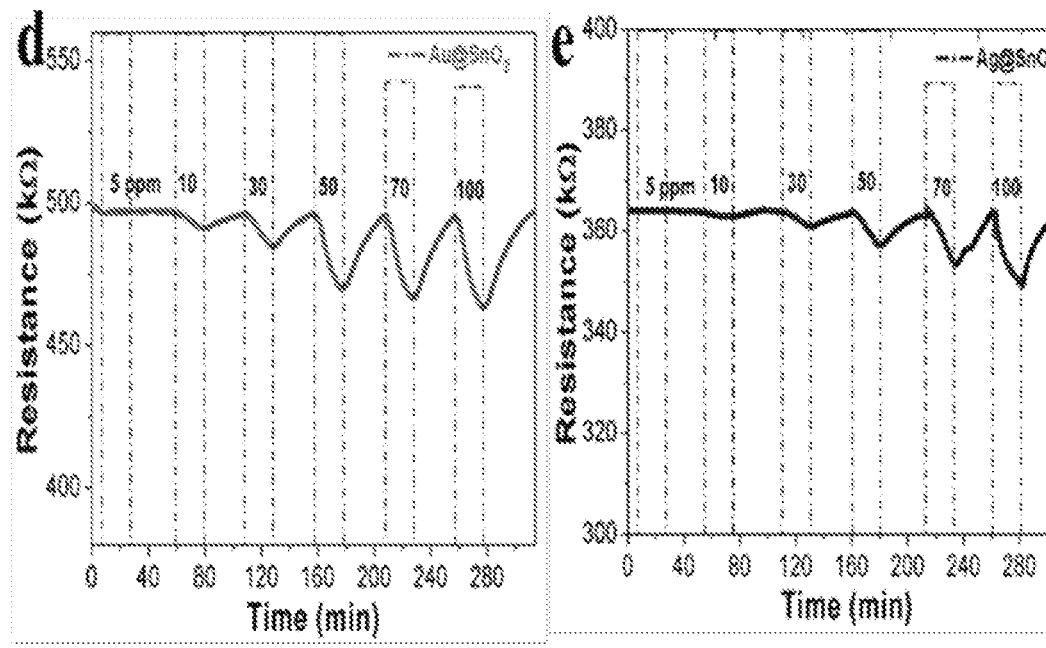
FIG. 6D shows the resistance of Au decorated $SnO_2$ thin films under different concentrations of hydrogen in accordance with certain embodiments of the present disclosure.
FIG. 6E shows the resistance of Ag decorated $SnO_2$ thin films under different concentrations of hydrogen in accordance with certain embodiments of the present disclosure.

FIG. 6A shows sensitivities of Pt decorated $SnO_2$ thin films with a thickness of 5, 10, 15 and 20 nm under hydrogen versus time. At 2000 ppm $H_2$, the Pt decorated $SnO_2$ thin film with the thickness of 15 nm shows the highest sensitivity among them.

Figure 6F:
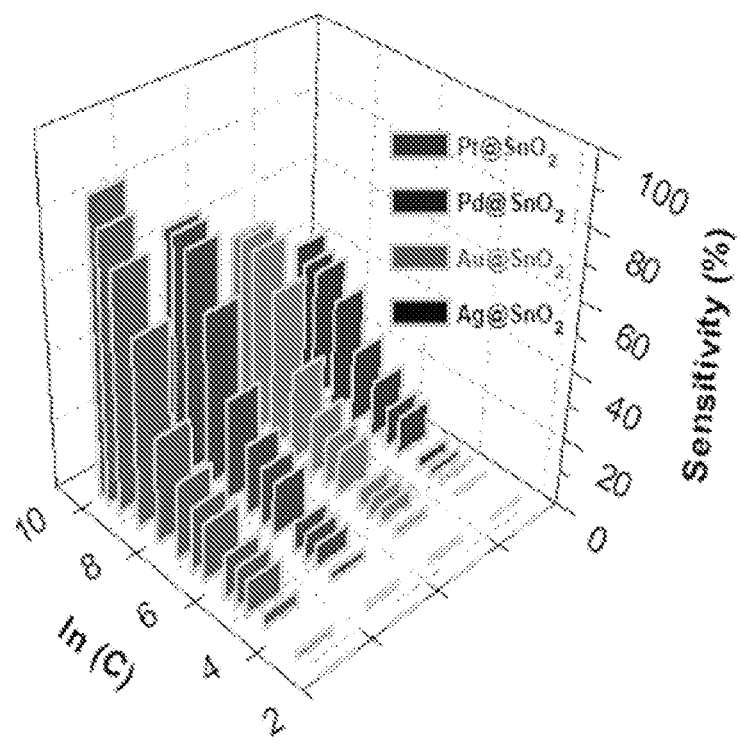
FIG. 6F shows sensitivities of the Pt, Pd, Au and Ag-decorated $SnO_2$ thin films of FIGS. 6B-6E under different concentrations of hydrogen.

FIGS. 6B-6E shows resistances of Pt, Pd, Au and Ag-decorated $SnO_2$ thin films, respectively under different concentrations of hydrogen. The Pt, Pd, Au and Ag-decorated $SnO_2$ thin films show different resistances under the same concentrations of hydrogen. The change of their resistances under different concentrations of hydrogen is different that means the Pt, Pd, Au and Ag-decorated $SnO_2$ thin films provide different sensitivities under the same concentration of hydrogen. Based on the results obtained from FIGS. 6B-6E, the sensitivities of the Pt, Pd, Au and Ag-decorated $SnO_2$ thin films under different concentrations of hydrogen are summarized and plotted as FIG. 6F.

FIG. 7A shows that the Pt, Pd, Au and Ag-decorated $SnO_2$ thin films provide different resistances under the same concentration of formaldehyde. FIG. 7D shows that the Pt, Pd, Au and Ag-decorated $SnO_2$ thin films provide different sensitivities under different concentrations of formaldehyde.

FIG. 7B shows that the Pt, Pd, Au and Ag-decorated $SnO_2$ thin films provide different resistances under the same concentration of toluene. FIG. 7E shows that the Pt, Pd, Au and Ag-decorated $SnO_2$ thin films provide different sensitivities under different concentrations of toluene.

FIG. 7C shows that the Pt, Pd, Au and Ag-decorated $SnO_2$ thin films provide different resistances under the same concentration of $NO_2$. FIG. 7F shows that the Pt, Pd, Au and Ag-decorated $SnO_2$ thin films provide different sensitivities under different concentrations of $NO_2$.

Figure 8:
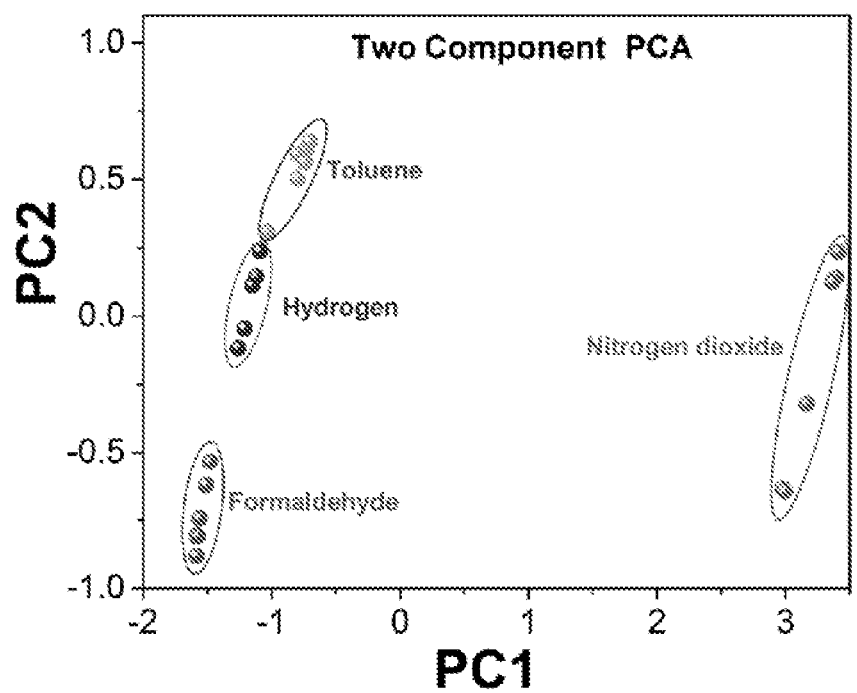
FIG. 8 shows a 2-component principal component analysis with Pt, Pd, Au and Ag-decorated $SnO_2$ thin films for hydrogen, formaldehyde, toluene and $NO_2$ in accordance with certain embodiments of the present disclosure.

According to different sensitivities of the Pt, Pd, Au and Ag-decorated $SnO_2$ thin films with a thickness of 15 nm under different concentrations of hydrogen, formaldehyde, toluene and $NO_2$, a principal component analysis is performed for effectively identifying the types and concentration of the above environmental gases. As shown in FIG. 8, the recorded four-dimensional data (corresponding to four kinds of gas sensors) is reduced to two-dimensional by PCA, which is used to visualize the sensitivity's Euclidean distance and relatedness intuitively among gas species. It shows that each gas has its own cluster area as circled which can be clearly distinguished. Each point refers to the PCA treated sensitivity of each metal-decorated gas sensor. The points fallen in a first loop refer to the detected gas being hydrogen, the points fallen in a second loop refer to the detected gas being formaldehyde, the points fallen in a third loop refer to the detected gas being toluene, the points fallen in a fourth loop refer to the detected gas being $NO_2$.

In certain embodiments, sensitivities of different metal-decorated metal oxide gas sensors under different gases and the corresponding concentration are predetermined and the results are stored in a memory for performing principal component analysis by an MCU during the actual gas detection having different sensitivities provided by different gas sensors in response to the detected gas species.

Apart from the principal component analysis, other pattern recognition techniques (e.g., support vector machine algorithms, artificial neural networks, et al.) can be used with the present gas sensor array for gas detection in certain embodiments.

Figure 9A:
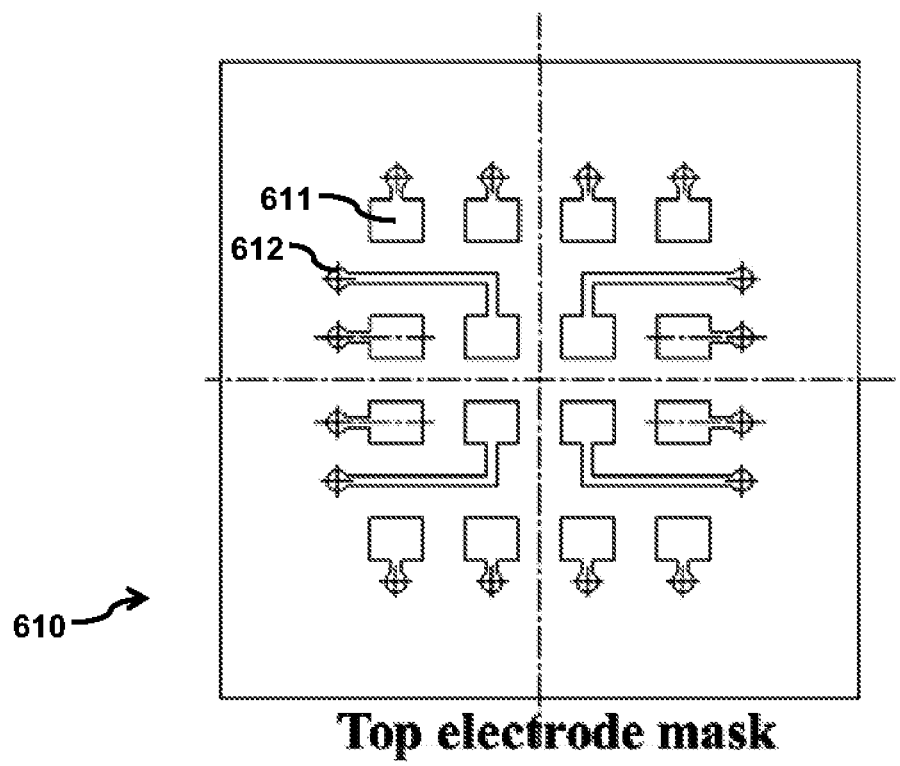
FIG. 9A is a top view of the electrode mask in accordance with certain embodiments of the present disclosure.
Figure 9B:
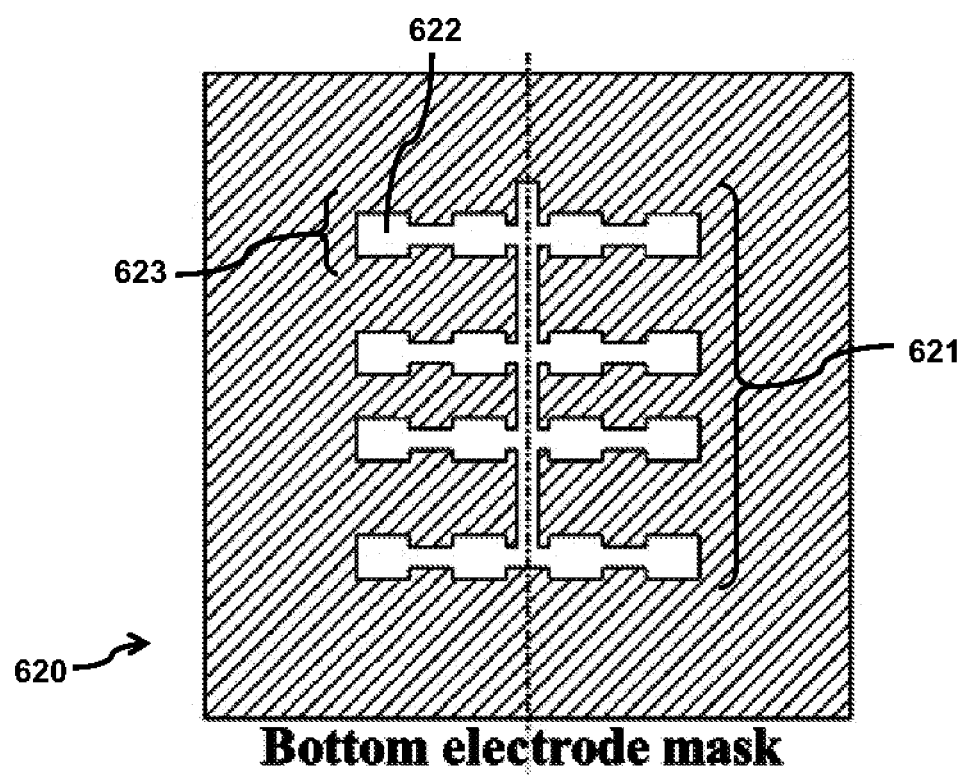
FIG. 9B is a bottom view of the electrode mask in accordance with certain embodiments of the present disclosure.

FIGS. 9A and 9B show the designs of a top electrode mask 610 and a bottom electrode mask 620 for sputtering deposition. The top electrode mask 610 has a predetermined mask pattern comprising a plurality of first electrode patterns 611 and a plurality of connection patterns 612. Each first electrode pattern 611 is connected to a connection pattern 612. The bottom electrode mask 620 has another predetermined mask pattern comprising a plurality of second electrode patterns 622. The second electrode patterns 622 on the same row are interconnected to each other to form an electrode serial 623, and all the electrode serials 623 are interconnected to each other to form a bottom pattern 621. The drawings illustrate an embodiment of the present disclosure for depositing 4×4 electrodes. Therefore, there are 16 first electrode patterns 611 arranged in four rows and four columns on the top electrode mask 610, and 16 second electrode patterns 622 arranged in four rows on the bottom electrode mask 620. It would be apparent to those skilled in the art that the mask may be patterned for depositing other numbers of electrodes, such as 1×1, 10×10, 2×8, etc. The first and second electrode patterns 611, 622 may have a rectangular shape, a square shape, a triangular shape, a quadrangular shape, a diamond shape, a polygonal shape, or any suitable shape. In certain embodiments, the first and second electrode patterns 611, 622 may have the shape of a 2.0 mm×2.5 mm rectangle.

Figure 10:
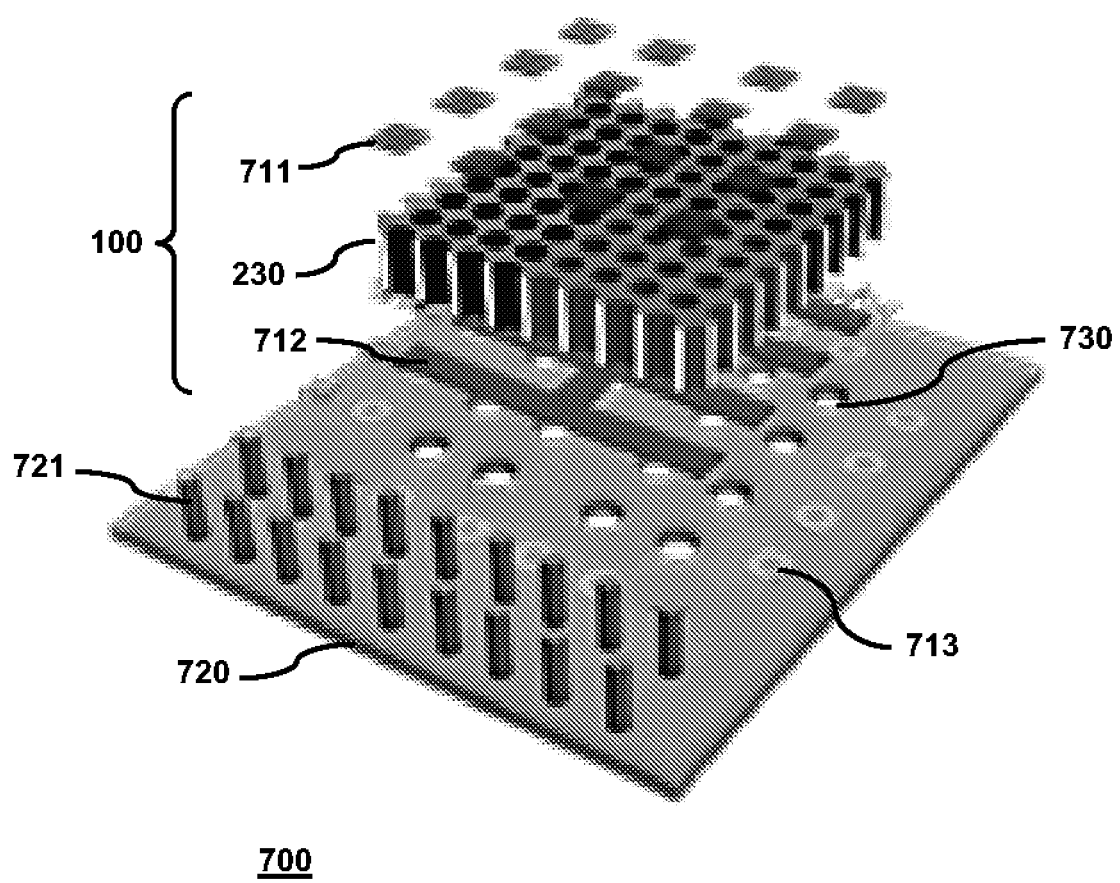
FIG. 10 is an exploded perspective view of the gas sensor unit in accordance with certain embodiments of the present disclosure.

The top electrode mask 610 and the bottom electrode mask 620 are shadow masks used to perform deposition, such as sputtering deposition, on the top and bottom surface of the gas-sensing substrate 230. Therefore, the gas sensor array 100, as detailed above, comprises one or more metal-decorated gas-sensing substrate 230 for performing gas detection and concentration level identification, a plurality of electrodes and a common plane. The deposition material can be Au or other noble metal. The Au layer deposited may have a thickness in the range of 10 nm to 500 nm, or preferably a thickness of 100 nm. As shown in FIG. 10, a plurality of top electrodes 711 are sputtered on the top surface of the metal-decorated gas-sensing substrate 230, and a common ground (GND) plane 712 is sputtered on the bottom surface of the metal-decorated gas-sensing substrate 230.

After depositing Au electrodes, the gas sensor array 100 is packaged on a sensor printed circuit board (PCB) 720 by connecting the plurality of top electrodes 711 and the common GND plane 712 to the signal channel pads 713 on the sensor PCB 720 using bond wires 714 to obtain a gas sensor unit 700. The bond wires 714 (shown in FIG. 11B) may be Cu wire, Au wire, or wire of other suitable alloy or metal. The sensor PCB 720 may be an application-specific PCB for a particular kind of gas sensor array 100, which comprises a plurality of airflow orifices 730 positioned under the gas sensor array 100 for allowing an airflow passage through the airflow orifices 730 into the gas sensor array 100 for gas leakage detection. The airflow orifices 730 may have a round shape, a rectangular shape, a square shape, a triangular shape, a quadrangular shape, or any suitable shape.

Figure 11A:
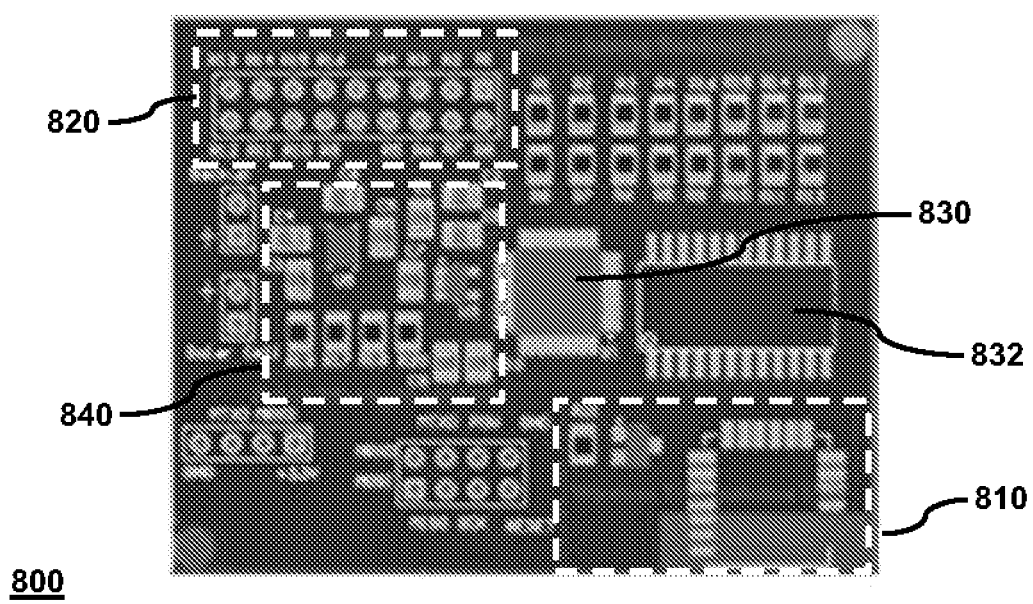
FIG. 11A is an image of the main PCB for connecting the gas sensor unit in accordance with certain embodiments of the present disclosure.
Figure 11B:
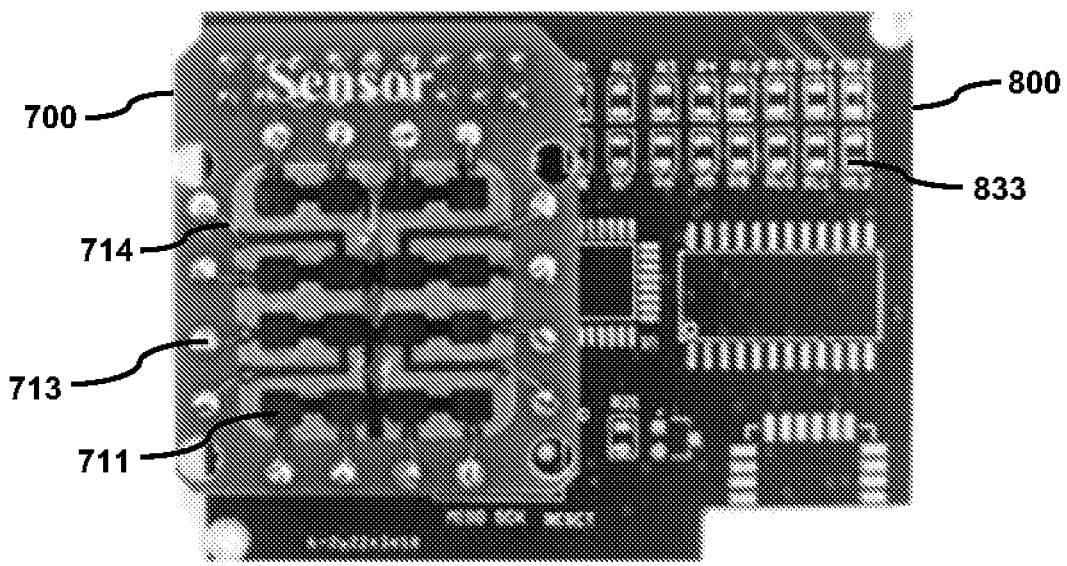
FIG. 11B is an image of the main PCB connected to the gas sensor unit of FIG. 11A.

The gas sensor unit 700 is further connected to a main PCB 800, which is shown in FIG. 11A. The main PCB 800 is an integrated PCB comprises circuitry for a transmission unit 810, a microcontroller unit (MCU) 830, and a power management unit 840, which can perform data readout, data processing, and transmission. The gas sensor unit 700 is electrically connected to the main PCB 800 by connecting the connector pins 721 to the socket 820. FIG. 11B shows the main PCB 800 connected to the gas sensor unit 700, wherein the gas sensor unit 700 is placed above the main PCB 800.

Figure 12:
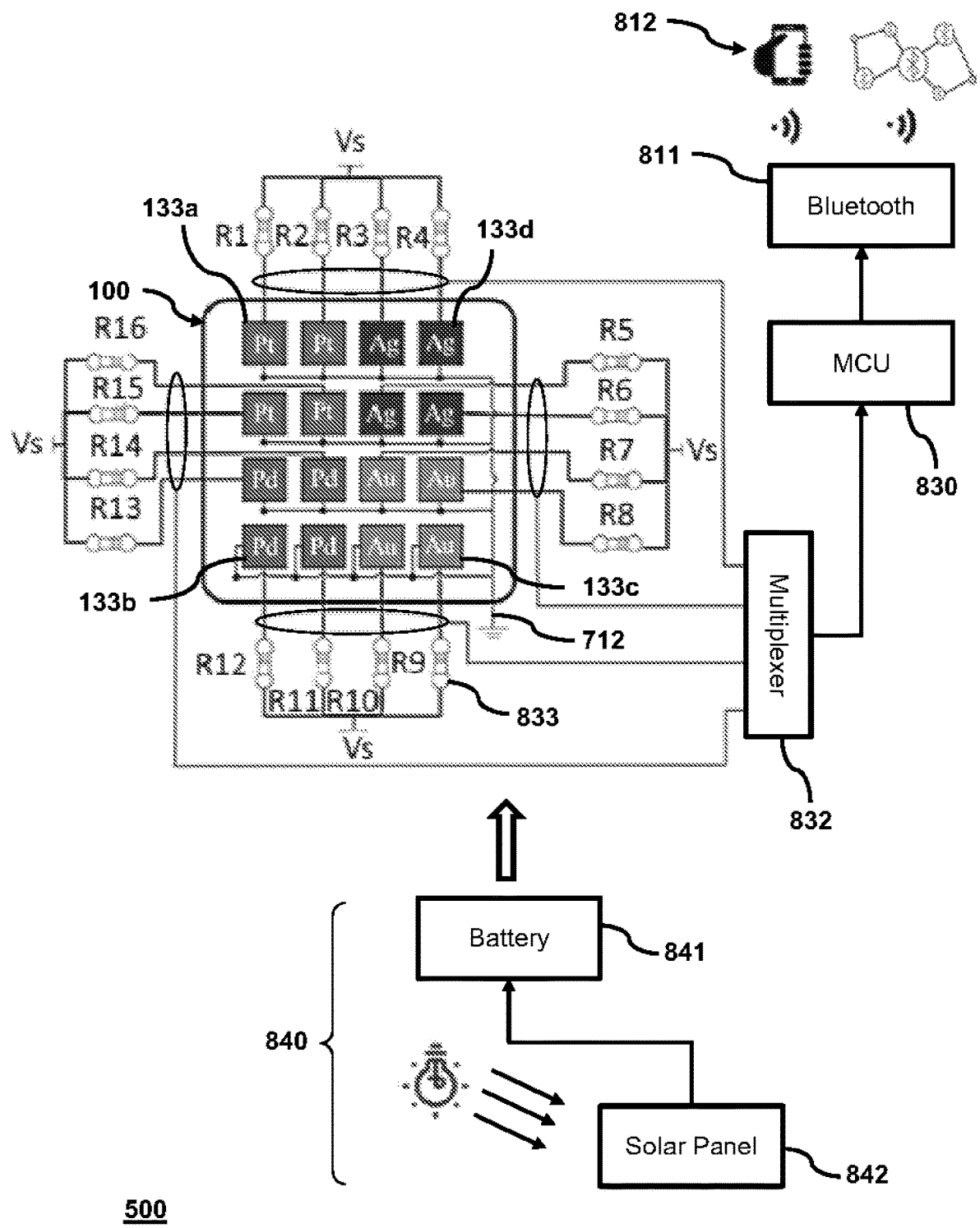
FIG. 12 is a schematic of the gas detecting apparatus in accordance with certain embodiments of the present disclosure.

FIG. 12 depicts the schematic of the gas detecting apparatus 500 in accordance with certain embodiments of the present disclosure. The gas detecting apparatus 500 is an Internet of Things (IoT) device, which includes a transmission unit 810, an MCU 830, and a power management unit 840, and a gas sensor unit 700. The gas sensor unit 700 is formed by packaging the gas sensor array 100 on a sensor PCB 720, wherein the gas sensor array 100 comprises a plurality of electrodes, and a common plane for connecting to the sensor PCB 720. The gas sensor array 100 may be separated into four regions, each decorated with Pt, Pd, Au and, Ag respectively for detecting the existence of a particular gas. According to different sensitivities of the Pt, Pd, Au, and Ag-decorated $SnO_2$ thin films under different concentrations of hydrogen, formaldehyde, toluene and $NO_2$, the MCU 830 is configured to perform the principal component analysis, a support vector machine algorithm, or an artificial neural network, for effectively identifying the types and concentration of the environmental gases. The four regions are the Pt-decorated gas-sensing region 133a, the Pd-decorated gas-sensing region 133b, the Au-decorated gas-sensing region 133c, and the Ag-decorated gas-sensing region 133d. A supply voltage Vs is provided to each individual top electrode 711 via a sensing resistor 833. The multiplexer 832 is configured to receive the sense voltage across each top electrode 711 in the gas sensor array 100 sequentially based on a clock signal, thereby the sense voltage across the Pt-decorated gas-sensing region 133a, the Pd-decorated gas-sensing region 133b, the Au-decorated gas-sensing region 133c, and the Ag-decorated gas-sensing region 133d can be obtained and coupled the sense voltage to the MCU 830. It is apparent that the multiplexer 832 and the sensing resistor 833 may be connected between the metal-decorated gas-sensing substrate 230 and the ground common GND plane 712 without departing from the spirit and scope of the present disclosure. The resistance of the plurality of sensing resistors 833 may be different as the sensitivity of each region may be different.

The MCU 830 is configured to receive the signals from the multiplexer 832, which include the sense voltages at the top electrodes 711 in the gas sensor array 100. A clock synchronization signal may also be provided by the multiplexer 832 to the MCU 830. The MCU 830 may also compute the sensitivity of the gas exposed with the variation of the digital values as compared with the sensitivities of the gases analyzed in algorithms. Therefore, the MCU 830 can identify and quantitatively detect the gas species in the environment by using principal component analysis, thereby determines if the concentration level is safe or not. The MCU 830 may perform further data optimization on the received signal, such as indexing, noise reduction, filtering, compression, deduplication, and data encoding. In the illustrated example, the MCU 830 collects the voltage signal from the 16 sensors obtained from the 16 channels via the multiplexer 832. The MCU 830 may comprise an analog-to-digital converter for converting the sense voltage into digital values. The digital values are then coupled to the Bluetooth low energy module 811 of the transmission unit 810 for communicatively transmitting the digital values to one or more receiving terminals 812. Alternatively, the transmission unit 810 may be configured to support one or more communication protocols for communicating with the receiving terminal 812, the one or more communication protocols being selected from Bluetooth, Wireless Body Area Network (WBAN), Ethernet, inter-integrated circuit ($I^2C$), and serial (COM) communication, and other communication protocols. The receiving terminals 812 may include a smartphone, smartwatch, tablet, personal digital assistant (PDA), laptop, desktop computer, other electronic devices, or cloud database.

In certain embodiments, the power management unit 840 of the gas detecting apparatus 500 comprises a solar panel 842 and a rechargeable battery 841. The solar panel 842 may include a 40 mm×110 mm solar cell for harvesting the indoor light energy. The harvested energy is used to power the gas detecting apparatus 500 and also continuously charge the rechargeable battery 841. In certain embodiments, the solar panel 842 may be a build-in module placed on one or more surface of the case of the gas detecting apparatus 500, or a separated module connected to the gas detecting apparatus 500. Therefore, the gas detecting apparatus 500 can be installed anywhere in an indoor area where there is light. The rechargeable battery 841 of the power management unit 840 may be a lithium-ion battery, a lead-acid battery, a nickel-cadmium battery, or a nickel-metal hydride battery. Preferably, the rechargeable battery 841 is a lithium-ion battery with at least 800 mAh capacity. Advantageously, the gas sensor array 100 only consumes an average power of 4.3 µW, which is less than a thousandth of the power consumption of a commercial $SnO_2$ thin film sensor. Therefore, the rechargeable battery 841 can operate efficiently with ultra-low power consumption to achieve an infinite lifetime monitoring using the solar panel 842. Further, the rechargeable battery 841 can compensate for the intermittency of light illumination in the dark conditions and night times, which offer stable power supply for the gas detecting apparatus 500 for operating without an external power source. In certain embodiments, the power management unit 840 may include an input power socket arranged to receive an electrical power supply for charging the rechargeable battery 841 and powering the gas detecting apparatus 500.

Figure 13:
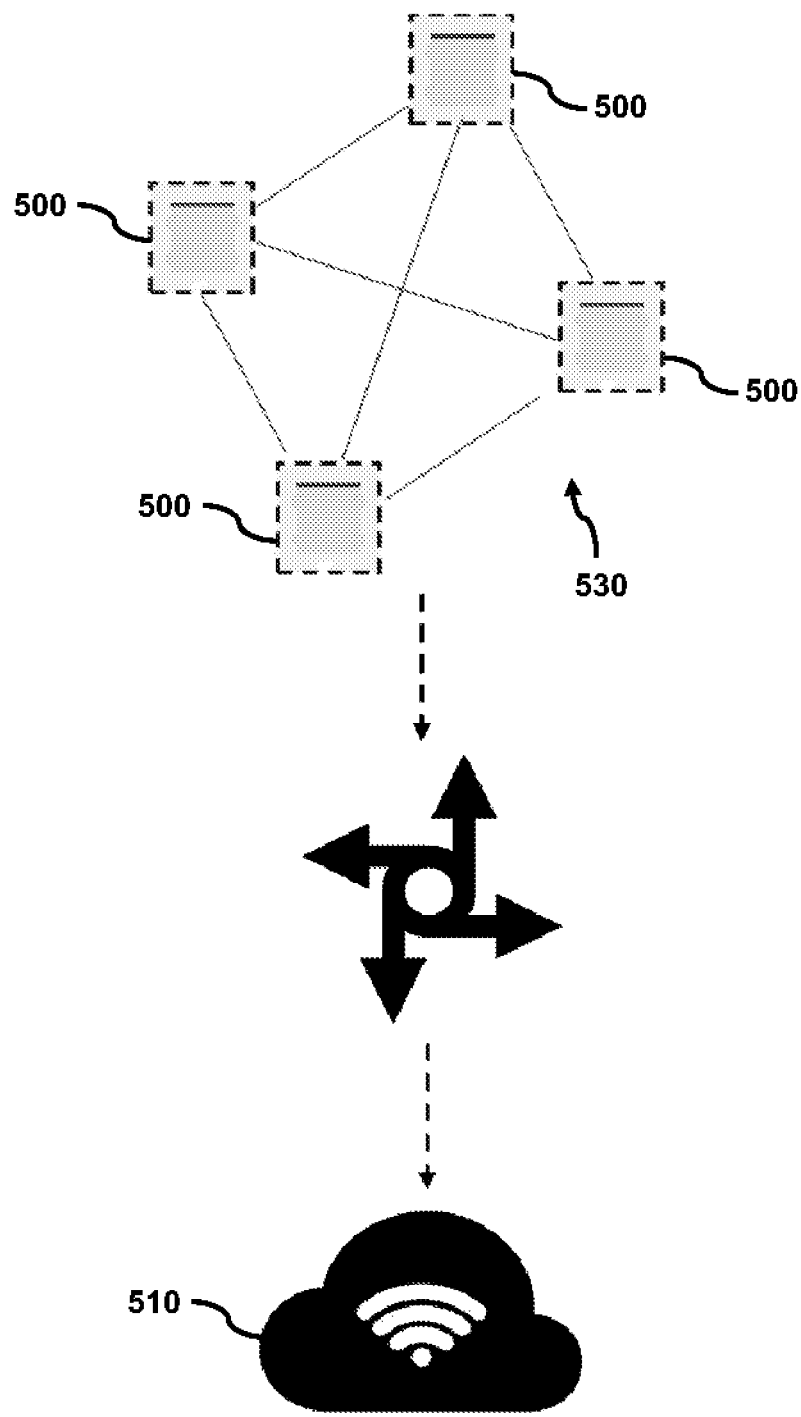
FIG. 13 is a simplified system diagram illustrating the connection of the gas detecting apparatus of FIG. 12.

FIG. 13 is a simplified system diagram illustrating the connection of the gas detecting apparatus 500 in accordance with certain embodiments of the present disclosure. A plurality of gas detecting apparatuses 500 may be connected together to form a mesh network 530, thereby the sensed data can be exchanged. Each gas detecting apparatus 500 operates as an IoT device, which may be communicatively connected to a cloud database 510 at a designated server through the Bluetooth low energy module 811 or using other communication protocols. It should also be understood that the data communication to the cloud database 510 may be a direct connection or indirectly through a mobile phone or other computer devices.

Figure 14:
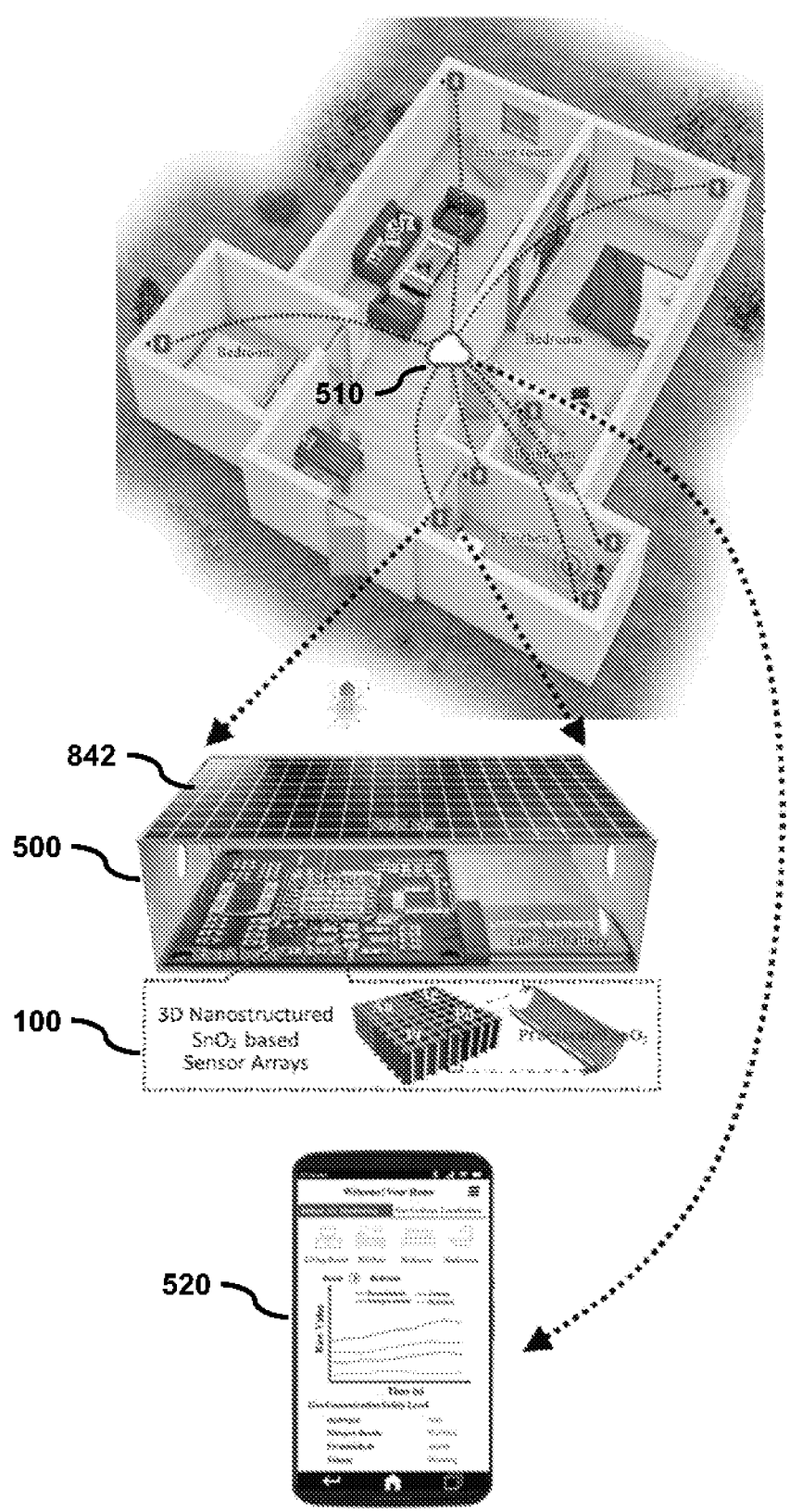
FIG. 14 is an exemplary smart home configuration using the gas detecting apparatus of FIG. 12.

FIG. 14 is an exemplary smart home configuration using the gas detecting apparatus 500 in accordance with certain embodiments of the present disclosure. Each gas detecting apparatus 500 is a self-powered sensing apparatus with a solar panel 842 positioned on an exterior surface of the gas detecting apparatus 500 for harvesting the indoor light energy. As illustrated in the example, the gas detecting apparatuses 500 are deployed in various locations in the smart home, such as the living room, kitchen, bedroom, and bathroom. In order to improve the detection of any gas leakage in the kitchen, four gas detecting apparatuses 500 are installed. Preferably, at least one gas detecting apparatus 500 is installed for a region of 10 square meters to ensure good coverage. Each gas detecting apparatus 500 is configured to capture the signals and recognize the complex gaseous environment (such as $H_2$, $NO_2$, formaldehyde, and toluene).

The installation of multiple gas detecting apparatuses 500 in a smart home can expand the indoor detection range and enable a tracing of the source of pollutants. With a continuous monitoring of the measured data, predictive analysis and trend analysis can also be performed to minimize the risk of false alarm. The captured signals are transmitted to the cloud database 510 at a designated server through the transmission unit 810. The transmission unit 810, preferably the Bluetooth low energy module 811 is configured to build up a communicative connection between the gas detecting apparatus 500 and a mobile phone for timely remote monitoring and distinguishing of gases, plotting of a geographical distribution map, and tracing of the gas leakage source in the smart home configuration.

As the MCU 830 of the gas detecting apparatus 500 can identify the gas species and the respective concentration level, the MCU 830 can determine if the concentration level is safe or not by matching and threshold comparison. In certain embodiments, the gas detecting apparatus 500 may include an alert system to provide sound warning in the event of suspected gas leakage. The information with respect to the gas species, concentration level, and voltage signals are sent to the mobile phone or cloud database 510 via the transmission unit 810. The information may be shown in a mobile application 520, and may generate an alert to the user to indicate a potential gas leakage. The alert can also be made through a computer network or by wireless transmission to other electronic devices, and provide a notification in the form of a pop-up message in the mobile application 520, an automatically generated e-mail, or a short message service (SMS). The mobile application 520 may also include a threshold selector for setting the threshold for each gas species and the acceptable range of concentration level, and thereby the alert is only provided when the detected concentration exceeds the predetermined threshold.

This illustrates the fundamental structure of a gas sensor array and a gas detecting apparatus incorporating the same in accordance with the present disclosure. It will be apparent that variants of the above-disclosed and other features and functions, or alternatives thereof, may be combined into many other different structures or apparatuses. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

What is claimed is:

1. A gas sensor array comprising:
   a gas-sensing substrate comprising:
   a three-dimensional (3D) porous template made of an electrically insulating material, having a top surface and a bottom surface and comprising a plurality of first pores and a plurality of second pores;
   a plurality of first metal-decorated metal oxide films, each first metal-decorated metal oxide film being electrically conductive and comprising a first metal oxide film and first metal decoration particles, the first metal oxide film having a first internal surface and a first external surface, the first internal surface attaching on an interior wall of a respective first pore, the external surface being decorated with the first metal decoration particles; and
   a plurality of second metal-decorated metal oxide films, each second metal-decorated metal oxide film being electrically conductive and comprising a second metal oxide film and second metal decoration particles, the second metal oxide film having a second internal surface and a second external surface, the second internal surface attaching on an interior wall of a respective second pore, the second external surface being decorated with the second metal decoration particles;

wherein the first metal decoration particles and the second metal decoration particles are made of different metals such that each first metal-decorated metal oxide film and each second metal-decorated metal oxide film provide different resistances in response to a gas at a concentration such that a first gas sensor formed of respective first metal-decorated metal oxide films and a second gas sensor formed of respective second metal-decorated metal oxide films provide different sensitivities in response to the gas at the concentration for enhancing accuracy of gas identification based on a pattern recognition technique, wherein the first metal oxide film is made of tin dioxide ($SnO_2$) with a thickness from 10 nm to 20 nm.

2. The gas sensor array of claim 1, wherein:

the 3D porous template further comprises a plurality of third pores and a plurality of fourth pores; and the gas-sensing substrate further comprises:

a plurality of third metal-decorated metal oxide films, each third metal-decorated metal oxide film being electrically conductive and comprising a third metal oxide film and third metal decoration particles, the third metal oxide film having a third internal surface and a third external surface, the third internal surface attaching on an interior wall of a respective third pore, the third external surface being decorated with the third metal decoration particles; and a plurality of fourth metal-decorated metal oxide films, each fourth metal-decorated metal oxide film being electrically conductive and comprising a fourth metal oxide film and fourth metal decoration particles, the fourth metal oxide film having a fourth internal surface and a fourth external surface, the fourth internal surface attaching on an interior wall of a respective fourth pore, the fourth external surface being decorated with the fourth metal decoration particles;

wherein the first metal decoration particles, the second metal decoration particles, the third metal decoration particles and the fourth metal decoration particles are made of different metals such that each first metal-decorated metal oxide film, each second metal-decorated metal oxide film, each metal-decorated metal oxide film and each fourth metal-decorated metal oxide film provide different resistances in response to a gas at a concentration such that the first gas sensor, the second gas sensor, a third gas sensor formed of respective third metal-decorated metal oxide films and a fourth gas sensor formed of respective fourth metal-decorated metal oxide films provide different sensitivities in response to the gas at the concentration for enhancing accuracy of gas identification based on the pattern recognition technique.

3. The gas sensor array of claim 2, wherein the first metal decoration particles are made of a first metal selected from a group consisting of Pt, Ag, Pd, Au, Ni, Cu, Ir and Ru; the second metal decoration particles are made of a second metal selected from a group consisting of Pt, Ag, Pd, Au, Ni, Cu, Ir and Ru; the third metal decoration particles are made of a third metal selected from a group consisting of Pt, Ag, Pd, Au, Ni, Cu, Ir and Ru; and the fourth metal decoration particles are made of a fourth metal selected from a group consisting of Pt, Ag, Pd, Au, Ni, Cu, Ir and Ru.

4. The gas sensor array of claim 2, wherein each of the first metal decoration particles, the second metal decoration particles, the third metal decoration particles and the fourth metal decoration particles has a diameter between 1 nm and 50 nm.

5. The gas sensor array of claim 2, wherein the second metal oxide film, the third metal oxide film and the fourth metal oxide film are made of a metal oxide selected from a group consisting of titanium dioxide ($TiO_2$), zinc oxide (ZnO), nickel(II) oxide (NiO) and iron(III) oxide ($Fe_2O_3$); and each of the second metal oxide film, the third metal oxide film and the fourth metal oxide film has a thickness between 1 nm and 100 nm.

6. The gas sensor array of claim 2, wherein the plurality of first pores is located in a first region of the 3D porous template; the plurality of second pores is located in a second region of the 3D porous template, the plurality of third pores is located in a third region of the 3D porous template; and the plurality of fourth pores is located in a fourth region of the 3D porous template.

7. A gas detecting apparatus, comprising:
a transmission unit;
a microcontroller unit (MCU);
a power management unit; and
a gas sensor unit formed by packaging the gas sensor array of claim 2 on a sensor printed circuit board (PCB), wherein the gas sensor array comprises a plurality of electrodes and a common plane for connecting to the sensor PCB.

8. The gas detecting apparatus of claim 7, wherein:
the plurality of electrodes is deposited on a top surface of the gas sensor array by sputtering deposition using a top electrode mask; and
the common plane is deposited on a bottom surface of the gas sensor array by sputtering deposition using a bottom electrode mask.

9. The gas detecting apparatus of claim 7, wherein the MCU is configured to identify and quantitatively detect gas species in the environmental gas by performing the pattern recognition technique based on the different sensitivities provided by the first gas sensor, the second gas sensor, the third sensor and the fourth sensor in response to the detected gas species.

10. The gas detecting apparatus of claim 9, wherein the pattern recognition technique is a principal component analysis, a support vector machine algorithm, or an artificial neural network.

11. The gas detecting apparatus of claim 7 further comprising a multiplexer configured to receive a sense voltage across each of the plurality of electrodes sequentially based on a clock signal, and couple the sense voltages to the MCU.

12. The gas detecting apparatus of claim 11, wherein the MCU comprises an analog-to-digital converter for converting the sense voltage into digital values.

13. The gas detecting apparatus of claim 12, wherein the transmission unit comprises means for communicatively transmitting the digital values to one or more receiving terminals.

14. The gas detecting apparatus of claim 7, wherein the power management unit comprises a solar panel positioned on an exterior surface of the gas detecting apparatus for harvesting indoor light energy, and a rechargeable battery that is charged by the harvested indoor light energy.

15. A mesh network having a plurality of gas detecting apparatuses of claim 7 for a smart home configuration, wherein:

each gas detecting apparatus is communicatively connected to a cloud database at a designated server through the transmission unit; and
the plurality of gas detecting apparatuses are deployed in various locations in the smart home for detecting gas leakage with an indoor detection range.

16. The mesh network of claim 15, wherein each gas detecting apparatus is communicatively connected to a mobile phone for remote monitoring and distinguishing of gases, plotting of a geographical distribution map, and leakage source tracing in the smart home configuration.

17. The gas sensor array of claim 1, wherein the first metal decoration particles are made of a first metal selected from a group consisting of platinum (Pt), silver (Ag), palladium (Pd), gold (Au), nickel (Ni), copper (Cu), iridium (Ir) and ruthenium (Ru); and the second metal decoration particles are made of a second metal selected from a group consisting of Pt, Ag, Pd, Au, Ni, Cu, Ir and Ru.

18. The gas sensor array of claim 1, wherein the 3D porous template has a honeycomb-like structure and a thickness between 100 nm and 100 μm; the electrically insulating material is aluminium (III) oxide ($Al_2O_3$), silicon dioxide ($SiO_2$) or titanium dioxide ($TiO_2$); the plurality of first pores is aligned substantially parallel with each other; the plurality of second pores is aligned substantially parallel with each other; and each of the plurality of first pores and the plurality of second pores has a width between 100 nm and 1 μm.

19. The gas sensor array of claim 1 further comprising:
one or more first top electrodes and one or more first bottom electrodes, each first top electrode contacting respective first metal-decorated metal oxide films at the top surface, each first bottom electrode contacting respective first metal-decorated metal oxide films at the bottom surface thereby forming one or more first gas sensors; and
one or more second top electrodes and one or more second bottom electrodes, each second top electrode contacting respective second metal-decorated metal oxide films at the top surface, each second bottom electrode contacting respective second metal-decorated metal oxide films at the bottom surface thereby forming one or more second gas sensors.

20. A gas sensor array comprising:
a gas-sensing substrate comprising:
a first three-dimensional (3D) porous template made of a first electrically insulating material, having a first top surface and a first bottom surface and comprising a plurality of first pores;
a second 3D porous template made of a second electrically insulating material, having a second top surface and a second bottom surface and comprising a plurality of second pores;
a plurality of first metal-decorated metal oxide films, each first metal-decorated metal oxide film being electrically conductive and comprising a first metal oxide film and first metal decoration particles, the first metal oxide film having a first internal surface and a first external surface, the first internal surface attaching on an interior wall of a respective first pore; and
a plurality of second metal-decorated metal oxide films, each second metal-decorated metal oxide film being electrically conductive and comprising a second metal oxide film and second metal decoration particles, the second metal oxide film having a second internal surface and a second external surface, the second internal surface attaching on an interior wall of a respective second pore, the second external surface being decorated with the second metal decoration particles;
wherein the first metal decoration particles and the second metal decoration particles are made of different metals such that each first metal-decorated metal oxide film and each second metal-decorated metal oxide film provide different resistances in response to a gas at a concentration such that a first gas sensor formed of respective first metal-decorated metal oxide films and a second gas sensor formed of respective second metal-decorated metal oxide films provide different sensitivities in response to the gas at the concentration for enhancing accuracy of gas identification based on a pattern recognition technique,
wherein the first metal oxide film is made of tin dioxide (SnO) with a thickness from 10 nm to 20 nm.

* * * * *